(12) United States Patent
Foster et al.

(10) Patent No.: US 12,016,656 B2
(45) Date of Patent: Jun. 25, 2024

(54) CELLULAR IONIC ACTIVITY VISUALISATION

(71) Applicant: QuantuMed Pty Ltd, Wavell Heights (AU)

(72) Inventors: Peter Graham Foster, Hyde Park (AU); Jason Arya Varzaly, Wavell Heights (AU); Laird Alan Varzaly, Wavell Heights (AU)

(73) Assignee: QuantuMed Pty Ltd, Wavell Heights (AU)

( * ) Notice: Subject to any disclaimer, the term of this patent is extended or adjusted under 35 U.S.C. 154(b) by 508 days.

(21) Appl. No.: 17/388,078

(22) Filed: Jul. 29, 2021

(65) Prior Publication Data

US 2022/0110527 A1   Apr. 14, 2022

Related U.S. Application Data

(60) Provisional application No. 63/090,117, filed on Oct. 9, 2020.

(51) Int. Cl.
| | |
|---|---|
| A61B 5/00 | (2006.01) |
| A61B 1/00 | (2006.01) |
| A61B 5/283 | (2021.01) |
| A61B 5/367 | (2021.01) |
| G02B 21/00 | (2006.01) |

(52) U.S. Cl.
CPC ........ *A61B 5/0084* (2013.01); *A61B 1/00167* (2013.01); *A61B 1/00186* (2013.01); *A61B 1/00188* (2013.01); *A61B 5/283* (2021.01); *A61B 5/367* (2021.01); *G02B 21/0032* (2013.01); *G02B 21/006* (2013.01)

(58) Field of Classification Search
CPC ... A61B 1/00167; A61B 5/0084; A61B 5/283; A61B 5/6869; A61B 1/00186; A61B 5/0071; G02B 21/0032; G02B 21/0028
See application file for complete search history.

(56) References Cited

U.S. PATENT DOCUMENTS

| | | | |
|---|---|---|---|
| 4,785,815 A | 11/1988 | Cohen | |
| 4,981,138 A * | 1/1991 | Deckelbaum | A61B 18/24 |
| | | | 600/478 |

(Continued)

FOREIGN PATENT DOCUMENTS

| | | |
|---|---|---|
| EP | 1642526 A1 | 4/2006 |
| WO | WO2009073736 A1 | 6/2009 |

OTHER PUBLICATIONS

Jousset [Optical Recording Of Calcium Currents During Impulse Conduction in Cardiac Tissue, Neurophotonics, 2015]. (Year: 2015).*

(Continued)

*Primary Examiner* — Oommen Jacob
(74) *Attorney, Agent, or Firm* — Edlavitch Law PLLC

(57) ABSTRACT

Described herein are improved systems and methods for cellular ionic activity visualization. Specifically, for example, the systems and methods can observe and characterize biological ionic channel activity and subsequently detect, measure or manipulate a biological sample in the field of biological or medical sciences on the cellular level. Such a capability can be implemented across any type of biological cell which possesses ionic channels on the surface or contained within.

20 Claims, 14 Drawing Sheets

(56) References Cited

U.S. PATENT DOCUMENTS

| | | | |
|---|---|---|---|
| 5,419,312 A * | 5/1995 | Arenberg | A61B 1/042 600/549 |
| 5,673,695 A | 10/1997 | McGee et al. | |
| 5,673,704 A | 10/1997 | Marchlinski et al. | |
| 5,674,698 A | 10/1997 | Zarling et al. | |
| 7,015,444 B2 * | 3/2006 | Kawano | G02B 21/004 250/201.3 |
| 8,068,899 B2 * | 11/2011 | Llewellyn | A61B 1/00045 600/478 |
| 8,273,081 B2 | 9/2012 | Viswanathan | |
| 8,922,781 B2 * | 12/2014 | Tearney | G01B 9/02091 356/479 |
| 9,161,694 B2 * | 10/2015 | Schnitzer | A61B 5/0071 |
| 10,052,052 B2 * | 8/2018 | Novotny | G01N 21/49 |
| 10,194,804 B2 * | 2/2019 | Zuckerman | A61B 5/1455 |
| 2003/0187427 A1 * | 10/2003 | Gatto | A61B 5/417 600/101 |
| 2004/0061072 A1 * | 4/2004 | Gu | G02B 23/26 250/458.1 |
| 2006/0106375 A1 | 5/2006 | Werneth et al. | |
| 2007/0087445 A1 * | 4/2007 | Tearney | G01N 21/6408 436/172 |
| 2008/0205833 A1 * | 8/2008 | Fu | A61B 1/07 385/117 |
| 2008/0269847 A1 * | 10/2008 | Nemenov | A61N 5/0613 607/89 |
| 2009/0054791 A1 * | 2/2009 | Flusberg | A61B 5/0059 600/478 |
| 2009/0236541 A1 * | 9/2009 | Lomnes | A61B 1/0646 250/362 |
| 2009/0268010 A1 * | 10/2009 | Zhao | A61B 1/00194 348/E13.001 |
| 2012/0065521 A1 | 3/2012 | Richards-Kortum et al. | |
| 2013/0137944 A1 * | 5/2013 | Jeong | A61B 5/0068 600/431 |
| 2014/0018792 A1 | 1/2014 | Gang et al. | |
| 2015/0150475 A1 | 6/2015 | Varcoe | |
| 2015/0362427 A1 * | 12/2015 | Novotny | G01J 3/433 356/39 |
| 2015/0369733 A1 * | 12/2015 | Izutani | G01N 21/0303 356/338 |
| 2016/0235278 A1 * | 8/2016 | Goebel | G02B 23/2469 |
| 2017/0065198 A1 | 3/2017 | Ruppersberg | |
| 2017/0296139 A1 * | 10/2017 | Giaya | A61B 5/0261 |
| 2018/0014773 A1 * | 1/2018 | Barton | A61B 5/0066 |
| 2018/0132698 A1 * | 5/2018 | Galstian | A61B 5/0042 |
| 2022/0110527 A1 * | 4/2022 | Foster | G02B 21/006 |

OTHER PUBLICATIONS

Fedotov [Fiber-optic magnetic-field imaging, Optics Letters vol. 39, Issue 24, pp. 6954-6957 (2014)]. (Year: 2014).*

Jousset F, Rohr S. Optical recording of calcium currents during impulse conduction in cardiac tissue. Neurophotonics. Apr. 2015;2(2):021011.

Jennifer H. Hou et al. Simultaneous mapping of membrane voltage and calcium in zebrafish heart in vivo reveals chamber-specific developmental transitions in ionic currents. Front. Physiol., Sep. 11, 2014.

Dany S. Adams et al. General Principles for Measuring Resting Membrane Potential and Ion Concentration Using Fluorescent Bioelectricity Reporters. Cold Spring Harb Protoc. : 2012(4): 385-397. doi:10.1101/pdb.top067710.

Eitaro Aihara et al. In Vivo Epithelial Wound Repair Requires Mobilization of Endogenous Intracellular and Extracellular Calcium. JBC Papers in Press, Oct. 11, 2013, DOI 10.1074/jbc.M113.488098.

Chris D. Constantinides et al. Noninvasive Quantification of Total Sodium Concentrations in Acute Reperfused Myocardial Infarction Using 23Na MRI. Magnetic Resonance in Medicine 46:1144-1151 (2001).

Xiaohu Dong et al. Dual-Color Imaging of Magnesium/Calcium Ion Activities with Two-Photon Fluorescent Probes. dx. doi.org/10.1021/ac302210v | Anal. Chem. 2012, 84, 8110-8113.

Lisa Ebihara et al. The Initial Inward Current in Spherical Clusters of Chick Embryonic Heart Cells. J. Gen. Physiol. The Rockefeller University Press, 0022-1295/80/04/0437/20, 437, vol. 75 Apr. 1980 437-456.

Todd J. Herron et al. Optical Imaging of Voltage and Calcium in Cardiac Cells & Tissues. DOI: 10.1161/CIRCRESAHA.111.247494, Feb. 17, 2012.

Nurdan Ozkucur et al. Ion Imaging During Axolotl Tail Regeneration In Vivo. Developmental Dynamics 239:2048-2057, 2010.

Claudio D. Stern et al. Sodium transport and the control of epiblast polarity in the early chick embryo. J. Embryol. exp. Morph. 77, 73-98 (1983).

Lizhi Xu et al. 3D multifunctional integumentary membranes for spatiotemporal cardiac measurements and stimulation across the entire epicardium. Nat Commun. ; 5: 3329. doi:10.1038/ncomms4329.

T. Zeuthen et al. Intra- and extracellular gradients of electrical potential and ion activities of the epithelial cells of the rabbit Ileum in vivo recorded by microelectrodes. Phil. Trans. R. Soc. Lond. B. 71, 277-281 (1975) [277-281].

Raymond A. Frizzell et al. Sodium Chloride Transport by Rabbit Gallbladder. The Journal of General Physiology ⊇ vol. 65, 1975 ⊇ pp. 769-795.

* cited by examiner

CELLULAR IONIC ACTIVITY VISUALISATION

CROSS-REFERENCE TO RELATED APPLICATIONS

The present application claims the benefit of priority from U.S. Provisional Patent Application No. 63/090,117, filed on Oct. 9, 2020, and entitled "CELLULAR IONIC ACTIVITY VISUALISATION", the entire disclosure of which application is hereby incorporated herein by reference.

TECHNICAL FIELD

The present disclosure relates to cellular ionic activity visualization.

BACKGROUND

The field of electrophysiology involves measurements of voltage change or electric current on a wide variety of scales from single ion channel proteins to whole organs like the heart. Measurement techniques involve placing electrodes into various samples of biological tissue, either in vitro or in situ. There are three basic types of electrodes used in these measurements: including simple solid conductors, printed circuit board tracings and hollow glass pipettes filled with an electrolyte solution. Such techniques have some technical problems. This disclosure provides some technical solutions to such technical problems to improve the state of the art of cellular ionic activity visualization.

SUMMARY

Described herein are improved systems and methods for cellular ionic activity visualization. The systems and methods (or techniques) disclosed herein can provide specific technical solutions to at least overcome the technical problems mentioned in this application as well as other technical problems not described herein but recognized by those skilled in the art.

The present disclosure relates to systems and methods for observing and characterizing biological ionic channel activity and subsequently detecting, measuring or manipulating a biological sample in the field of biological or medical sciences on the cellular level. Such a capability can be implemented across any type of biological cell which possesses ionic channels on the surface or contained within. Of particular, but by no means exclusive, use in electrophysiology applications such as, but not limited to, mapping and characterizing the electrical activity or potential generated when cells are neurologically or otherwise activated.

Some embodiments of the present disclosure include an apparatus that includes a laparoscopic instrument, an optical source, a focusing element, and a fiber optic deliver system. The optical source is configured to emit an optical beam. The focusing element is configured to focus the optical beam into a fiber optic cable. The fiber optic delivery system is configured to be integrated into the laparoscopic instrument and provide ion channel activity measurement. And, the fiber optic delivery system includes the fiber optic cable, a fiber optic core, and a graded index lens. The fiber optic cable includes the fiber optic core. The graded index lens is configured to: contact a biological sample; focus a ray of light on the biological sample, wherein the ray of light is emanating from the fiber optic core; and produce an image of an interface at the graded index lens and the biological sample. The fiber optic core is configured to: transmit light to the graded index lens; and filter backscattered light reflected from the biological sample to select light from a field plane within the biological sample.

In some embodiments, the apparatus includes a computer system configured to determine a state and activity of ionic channels of a plurality of cells in the biological sample based on the image of the interface at the graded index lens and the biological sample.

In some embodiments of the apparatus, the fiber optic cable includes a plurality of fiber optic cores, and the plurality of fiber optic cores includes the fiber optic core, and the graded index lens is configured to: focus rays of light on the biological sample emanating from the plurality of fiber optic cores, wherein each one of the rays of light is emanating from a respective fiber optic core of the plurality of fiber optic cores; and produce respective images of respective interfaces at the graded index lens and the biological sample for each respective fiber optic core of the plurality of fiber optic cores to provide spatial discrimination within the biological sample. In such embodiments, each fiber optic core of the plurality of fiber optic cores is configured to: transmit light to the graded index lens; and filter backscattered light reflected from the biological sample to select light from a respective field plane within the biological sample. Also, in such embodiments, the apparatus can include a computer system configured to determine a state and activity of ionic channels of a plurality of cells in the biological sample, based on the respective images of the respective interfaces at the graded index lens and the biological sample for each respective fiber optic core of the plurality of fiber optic cores. Furthermore, the fiber optic delivery system can be in a confocal arrangement.

In some embodiments of the apparatus, the focusing element is a first light focusing element and the graded index lens is a second light focusing element. In such embodiments, the optical beam emitted from the optical source can be a collimated optical beam. Also, in such embodiments, the apparatus can include an optical scanning element configured to direct the optical beam into the fiber optic cable. Also, the graded index lens can be configured to capture scattered light in its production of the image of the interface at the graded index lens and the biological sample, and the scattered light captured by the graded index lens can be transmitted via an optical fiber of the fiber optic cable. Further, the apparatus can include a beam splitter, and wherein the scattered light, transmitted via the optical fiber, retraces a path of the optical beam before being reflected by the beam splitter. The apparatus can also include a pinhole and a third focusing element that is configured to focus the scattered light through the pinhole after the scattered light has been reflected by the beam splitter. The light focused through the pinhole can be used as input for the production of the image of the interface at the graded index lens and the biological sample. Also, the apparatus can include a fourth focusing element configured to direct the light focused through the pinhole onto a light detector of the apparatus.

In some embodiments of the apparatus, the fiber optic core includes a magnetic field sensitive diamond nitrogen-vacancy (NV) center. The magnetic field sensitive diamond NV center can be sandwiched between optically reflective coatings to provide an optical cavity for increasing optical field strength in the magnetic field sensitive diamond NV center. Also, the magnetic field sensitive diamond NV center can be attached to a distal end of the graded index lens.

Some embodiments of the present disclosure include a system including the aforesaid apparatus. Some embodiments of the present disclosure include a system having a laparoscopic instrument, an array of microscopic probes, an optical source, a focusing element, and a fiber optic delivery system. The array of microscopic probes is integrated into or delivered through the laparoscopic instrument and configured to measure electrical potential across a plurality of cells of a biological sample. The optical source is configured to emit an optical beam. The focusing element configured to focus the optical beam into a fiber optic cable. The fiber optic delivery system is configured to be integrated into the laparoscopic instrument and provide ion channel activity measurement, and the fiber optic delivery system includes the fiber optic cable, a fiber optic core, and a graded index lens. The fiber optic cable includes the fiber optic core. The graded index lens is configured to: contact the biological sample; focus a ray of light on the biological sample, wherein the ray of light is emanating from the fiber optic core; and produce an image of an interface at the graded index lens and the biological sample. The fiber optic core is configured to: transmit light to the graded index lens; and filter backscattered light reflected from the biological sample to select light from a field plane within the biological sample.

In some embodiments, the system includes a computer system configured to determine a state and activity of ionic channels of the plurality of cells in the biological sample based on the electrical potential across the plurality of cells of the biological sample and the image of the interface at the graded index lens and the biological sample. In such embodiments, the system can further include a microscopic device including the array of microscopic probes and wherein respective conductive tips of the array of microscopic probes sit flush with a surface of the microscopic device.

Some embodiments of the present disclosure include an apparatus including a cannula-based instrument, an optical source configured to emit an optical beam, a focusing element configured to focus the optical beam into a fiber optic cable, and a fiber optic delivery system, configured to be integrated into the cannula-based instrument and provide ion channel activity measurement. The fiber optic delivery system includes the fiber optic cable, a fiber optic core, and a graded index lens. The fiber optic cable includes the fiber optic core. The graded index lens is configured to: contact a biological sample; focus a ray of light on the biological sample, wherein the ray of light is emanating from the fiber optic core; and produce an image of an interface at the graded index lens and the biological sample. The fiber optic core is configured to: transmit light to the graded index lens; and filter backscattered light reflected from the biological sample to select light from a field plane within the biological sample.

Some embodiments of the present disclosure include a system including the aforesaid apparatus.

With respect to some embodiments, disclosed herein are computerized methods for cellular ionic activity visualization, as well as a non-transitory computer-readable storage medium for carrying out technical operations of the computerized methods. The non-transitory computer-readable storage medium has tangibly stored thereon, or tangibly encoded thereon, computer readable instructions that when executed by one or more devices (e.g., one or more personal computers or servers) cause at least one processor to perform a method for a novel and improved cellular ionic activity visualization.

With respect to some embodiments, a system is provided that includes at least one computing device configured to provide useful and novel cellular ionic activity visualization. And, with respect to some embodiments, a method is provided to be performed by at least one computing device. In some example embodiments, computer program code can be executed by at least one processor of one or more computing devices to implement functionality in accordance with at least some embodiments described herein; and the computer program code being at least a part of or stored in a non-transitory computer-readable medium.

BRIEF DESCRIPTION OF THE DRAWINGS

The present disclosure will be understood more fully from the detailed description given below and from the accompanying drawings of various embodiments of the disclosure.

DETAILED DESCRIPTION

Figure 1:
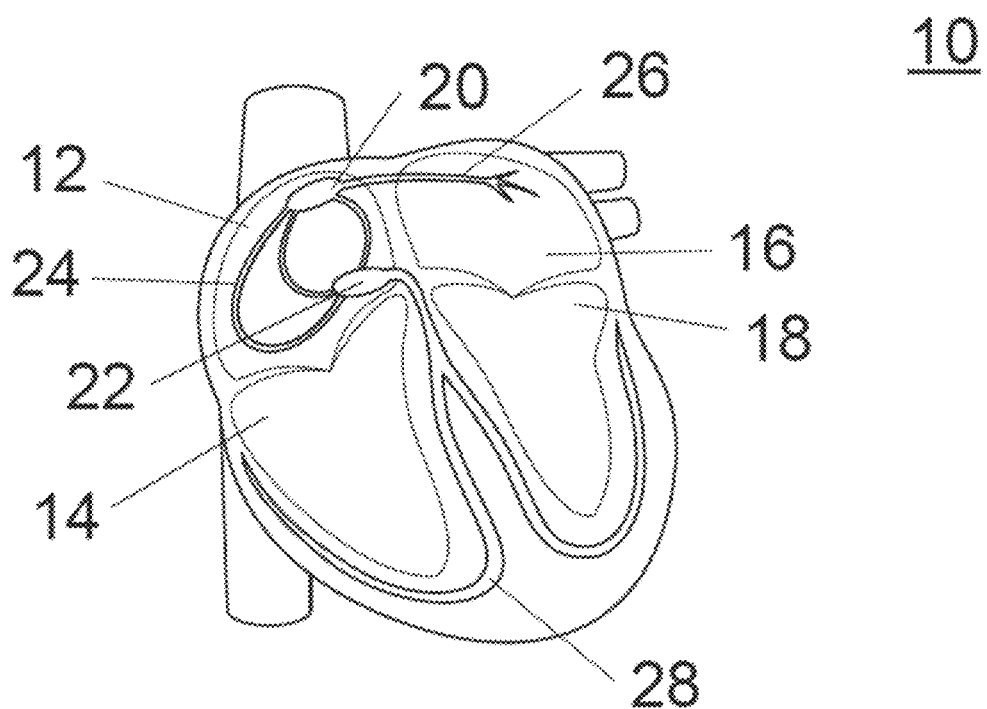
FIG. 1 illustrates a schematic representation of a human heart.

Described herein are improved systems and methods for cellular ionic activity visualization.

The field of electrophysiology involves measurements of voltage change or electric current on a wide variety of scales from single ion channel proteins to whole organs like the heart. Measurement techniques involve placing electrodes into various samples of biological tissue, either in vitro or in situ. There are three basic types of electrodes used in these measurements: including simple solid conductors, printed circuit board tracings and hollow glass pipettes filled with an electrolyte solution.

If an electrode is small enough (microns in diameter), then it can be inserted into a cell. In such a case, direct observation and recording of the intracellular electrical activity of a cell can be made. However, such invasive procedures will often rupture the cell membrane causing a leak of cell contents and reducing the life of the cell. Intracellular activity can also be observed using the hollow glass pipette electrode. In such a technique, the microscopic pipette tip is pressed against the cell membrane, to which it tightly adheres by an interaction between glass and lipids of the cell membrane. The cell membrane encircled by the tip of the pipettes is then ruptured allowing fluid continuity between the electrolyte and the cytoplasm but results in destruction of the cell during the measurement.

Action potentials can also be recorded by placing the electrode in contact with the extracellular space. If the tip of the electrode is small enough such a configuration can allow indirect observation and recording of action potentials from a cell. Depending on the preparation and precise electrode placement, an extracellular configuration can pick up the activity of several nearby cells simultaneously. As electrode size increases, the net activity of many cells is recorded. Still larger electrodes, such as uninsulated needles and surface electrodes are sensitive only to certain types of synchronous activity and measure the ensemble potential across millions of cells.

The extracellular patch clamp technique is a laboratory technique that allows the study of single or multiple ion channels in cells. Patch clamp recording uses a glass micropipette called a patch pipette as a recording electrode, and another electrode in the bath around the cell, as a reference ground electrode. Depending on what the researcher is trying to measure, the diameter of the pipette tip used can vary, but it is usually in the micrometer range. The pipette tip or other similar device is used to enclose a membrane surface area or "patch" that often contains just one or a few ion channel molecules. such a type of electrode is distinct from the "sharp microelectrode" used to puncture cells in traditional intracellular recordings, in that it is sealed onto the surface of the cell membrane, rather than inserted through it.

On a larger scale of observation, Electromyography (EMG) measures gross muscle electrical activity in response to muscle contraction. One or more small electrodes are inserted through the skin into the bulk of the muscle. An audio-amplifier can also be used so the activity can be heard. The action potential, the size and shape of the wave, provides information about the ability of the muscle to respond when the nerves are stimulated. As the muscle is contracted more forcefully, more and more muscle fibers are activated, producing a stronger overall bulk action potential response. Measured EMG potentials range from tens of microvolts to tens of millivolts depending on the muscle under observation.

There are two kinds of EMG: surface EMG and intramuscular EMG. Surface EMG assesses muscle function by recording muscle activity from the surface above the muscle on the skin. Surface electrodes are able to provide only a limited assessment of the muscle activity. Surface EMG can be recorded by a pair of electrodes or by a more complex array of multiple electrodes. More than one electrode is needed because EMG recordings display the potential difference between two electrodes.

The actual placement of an EMG electrode can be difficult and depends on a number of factors, such as specific muscle selection, the size of that muscle and the amount of superficial adipose tissue (fat). Proper electrode placement can be critical for accurate measurement of the muscle of interest. EMG is more effective on superficial muscles due to the difficulty of insulating the electrode from the action potentials of superficial muscles when measuring deeper muscles. Such factors can limit the value of EMG in diagnosis. Nevertheless, EMG is only suitable for providing information about bulk muscle electrical activity.

Intramuscular EMG can be performed using a variety of different types of recording electrodes. The simplest approach is a monopolar needle electrode. The electrode can be a fine wire inserted into a muscle with a surface electrode as a reference; or two fine wires inserted into muscle referenced to each other. Most commonly fine wire recordings are for research or kinesiology studies. Diagnostic monopolar EMG electrodes are typically stiff enough to penetrate skin and insulated, with only the tip exposed using a surface electrode for reference. Nevertheless, these methods can only probe a discrete number of points within the volume of the tissue. If one is to observe the detailed flow of electrical current through a given tissue sample, a wide-field, continuous (rather than discretely sampled) and preferably non-invasive method is used.

An electrolyte gradient across a cell membrane results in an electrical potential across the membrane and measurement of the gradient provides information about the state of electrical potential within the cell. The cellular ionic activity visualization system described herein can determine the state and activity of ionic channels of a plurality of cells in a biological sample, hereinafter referred to as cellular observation. such information allows then by observation determination of the electrolyte gradient, and thus the activity of a plurality of cells.

Some embodiments can include a method of detecting, measuring and monitoring the ionic channel activity with subsequent assessment of the electrical potential across a broad area of tissue. The method can be non-invasive and also can be non-destructive. The method can also be used in vivo and allow real time assessment.

The applications of the cellular ionic activity visualization system range across biological cellular activity systems. An example application of the system can map the electrical activity of the human heart. Cardiac muscle shares a few characteristics with skeletal muscle and smooth muscle, but it has some unique properties of its own. One of the most interesting of these exceptional properties is automaticity, its ability to initiate an electrical potential at a fixed rate that spreads rapidly from cell to cell via gap junctions to trigger the contractile mechanism resulting in the heart functioning as a pump and generating cardiac output. Even though cardiac muscle has automaticity, heart rate is modulated by the endocrine and nervous systems.

There are two major types of cardiac muscle cells: myocardial contractile cells and myocardial conducting cells. The myocardial contractile cell is a specialized muscle cell that is approximately 10-25 microns in diameter and about 100 microns in length. They constitute the bulk of the cells in the atria and ventricles (approximately 99%) and are responsible for contractions that pump blood through the body. The myocardial conducting cells have an increased rate of conduction, initiate and propagate the electrical potential that travels throughout the heart and triggers the contractions that propel the blood.

Each cardiac cell is capable of generating its own electrical impulse followed by a contraction. The cells with the highest intrinsic rate of activation/depolarization will naturally become the pace setter with conduction of the impulse triggering adjacent 'slower' cells to also contract.

Normal cardiac rhythm is established by the sinoatrial (SA) node, a specialized group of myocardial conducting cells located in the superior and anterior walls of the right atrium in close proximity to the orifice of the superior vena cava. The SA node has the highest inherent rate of depolarization and is known as the pacemaker of the heart. It initiates the sinus rhythm, or normal electrical pattern, which then propagates around the atrium through specialized internodal pathways to the atrioventricular (AV) node in a very specific pattern to provide the normal contraction of the heart.

The normal electrical conduction system of the heart allows the impulse that is generated by the SA of the heart to be propagated to and stimulate the myocardium (muscular layer of the heart). When the myocardium is stimulated, it contracts. It is the ordered stimulation of the myocardium that allows efficient contraction of the heart, thereby allowing blood to be pumped to the body. The coordinated function of the atria to deliver blood to the ventricles, followed by the coordinated function of the ventricles to generate cardiac output will here in be termed a normal heartbeat. However, in some instances, such as in the case known as Atrial Fibrillation (AF), the normal electrical propagation pathways get interrupted for a period causing irregular contraction of the heart muscle and, while not immediately fatal, can cause ongoing problems.

There are multiple theories about the etiology of atrial fibrillation. A useful theory is that, in atrial fibrillation, the regular impulses produced by the sinus node for a normal heartbeat are overwhelmed by rapid electrical discharges produced in the atria and adjacent parts of the pulmonary veins. Sources of these disturbances are either automatic foci, often localized at one of the pulmonary veins, or a small number of localized sources in the form of either re-entrant electrical spiral waves (rotors) or repetitive focal beats; these localized sources can be found in the left atrium near the pulmonary veins or in a variety of other locations through the left atrium and the right atrium.

Because recovery of the atria from excitation is heterogeneous, the electrical waves generated by the AF sources undergo repetitive, spatially distributed breakup and fragmentation in a process known as "fibrillatory conduction".

AF can be distinguished from atrial flutter, which appears as an organized electrical circuit usually in the right atrium. Atrial flutter produces characteristic saw-toothed F-waves of constant amplitude and frequency on an EEG whereas AF does not. In atrial flutter, the discharges circulate rapidly at rates of up to 300 beats per minute (bpm) around the atrium. In AF, there is no regularity of such a kind, except at the sources where the local activation rate can exceed 500 bpm, resulting in loss of atrial output.

Although the electrical impulses of AF can occur at a high rate, most of them do not result in a conducted heartbeat owing to the function of the AV node. A heartbeat results when an electrical impulse from the atria passes through the atrioventricular node to the ventricles and resulting in propagation of the impulse with resultant contraction. During AF, the multitudes of fibrillatory conductions are prevented from conducting through to the ventricular mass of the heart owing to the fibrous cardiac skeleton. The AV node represents the only physiological pathway from the atria to the ventricles and limits the number of conducted impulses that pass through, thus preventing the severe ventricular tachycardia that can result from the rapid atrial discharge associated with AF. Severe ventricular tachycardia can result in loss of cardiac output and subsequent death.

The cellular ionic activity visualization system can map electrical potentials and current flow in a biological sample. In some embodiments, the biological sample is the cardiac muscle. Knowledge of the electrical pathway can lead to a method of treating atrial fibrillation. Under normal conditions, ordered stimulation of the myocardium via defined internodal pathways of myocardial conducting cells allows efficient contraction of the heart. In electrical terms, the myocardial conduction pathway presents a low impedance to electrical flow and can be the conduction pathway.

However, if there is a point of localized higher impedance within the normal electrical pathway, the electrical signal will look for a lower impedance path, which can result in the observation of a noticeable 'short circuit' of the normal conduction system leading to less than optimal coordination of the muscle's contraction-atrial fibrillation. Observation of electrical flow branching outside of the normal conduction pathway can identify the source of an atrial fibrillation event.

The cellular ionic activity visualization system can locate localized high impedance points that could potentially lead to breakout of an otherwise normal cellular electrical conduction system, which in some embodiments can be applied to the cardiac system. In such embodiments, a method of locating high impedance points, that can be termed areas of delayed or slowed conduction by other sources, within the myocardial conduction cell pathways that result in electrical activity branching out from the normal conduction cell pathways and leading to atrial fibrillation. It can be appreciated by those skilled in the art that such a method is applicable and intended to be used in identifying areas where electrical activity deviates from the normal pathways in non-cardiac cells.

Sodium and potassium channels are ion-selective protein pores that span the cell's plasma membrane and serve to establish and regulate membrane potential. They are typically classified according to their response mechanism: voltage-gated channels open or close in response to changes in membrane potential. In excitable cells, such as neurons and myocytes, the channels of the cells function to create the action potential and to reset the cell's resting membrane potential.

The electrical flow through the cardiac muscle can be characterized by flow of ions across cell membranes. A steady-state, presumably 'resting' cardio myocyte has a resting cell membrane potential of the order of −80 millivolts (mV) to −90 mV. A myocyte contracts by undergoing a change in electrical potential via ion exchange between the intracellular and extracellular space, which may not be a simple exchange of one ion species, rather a complex multi-species process. Where the terms ion, electrolyte and similar terms are used in this disclosure they are to be read to include single-species and multi-species processes.

There are 5 phases of a myocyte contraction, typically labelled phase 0 through 4. Phase 4 is the steady-state, pre-contraction state. Sodium Na+ and calcium Ca2+ channels are closed while potassium K+ channels are kept open and regulate potential to roughly −80 mV. Phase 0 is defined as the onset of contraction when fast sodium channels open and the cell is rapidly flooded and with Na+ ions and then equally quickly flushed, resulting in a membrane potential the order of 10-20 mV, which can be within 3-5 milliseconds (ms). Phase 1 includes transient potassium channels opening to sweep potassium K+ ions from the cell and reduce membrane potential to zero. In phase 2 there is an influx of calcium Ca2+ ions which is electrically balanced by potassium K+ ions slowly leaving the cell over roughly 175 ms. In phase 3, calcium channels close but potassium channels remain open returning the membrane potential to its steady-state condition over roughly 75 ms.

The process of myocyte contraction can be considered as one full electrolyte cycle. Each cell type exhibits a different electrolyte cycle and indeed the difference provides a mechanism for characterizing and detecting functionally different cellular types within a biological sample. Consider the case a cancer cell within healthy tissue. It can exhibit a different electrolyte cycle due to its accelerated life cycle and division process. The process can then offer the opportunity to select specific target cells from a biological sample.

A laboratory-based animal study with the research performed on cultured cells to determine calcium ion currents is known. The technique is applicable in vitro and not described as, or leading to, a clinical, therapeutic or diagnostic tool. The authors of this disclosure are skilled in the art of physiology, specifically directed to the field of cell culture and fundamental cellular physiological processes) and also have skill in the art of optical physics. The cellular ionic activity visualization system draws on skills in the combined arts of cellular physiology, optical physics, electrical engineering, biomedical engineering and medicine, more specifically relating to cardiology, a field that relates to clinical treatment of cardiac issues and neurology. The cellular ionic activity visualization system can adapt these techniques to clinical outcomes in living biological systems and in particular in human anatomy and cardiology.

The cellular ionic activity visualization system can determine the relative intra- and extra-cellular ion concentrations and thereby determine the overall electrical flow through a biological sample by observing the temporal changes of intracellular ion concentration (or relative intra-extra-cellular concentration) across the sample. The cellular ionic activity visualization system applies determination of either static, periodic or aperiodic relative cellular ion concentrations or the various channels that control them. The determination can occur by monitoring the ionic channel activity within an area/volume of a biological sample by means of observing, for example, intracellular and extracellular concentration of calcium, sodium, potassium or other ionic components concentrations.

The aforementioned discussion centers on the detection or visualization of electro-potentials in biological samples. The cellular ionic activity visualization system goes beyond simple visualization. Visualization of biological sample electro-activity is the first step in creating a potential treatment process. The cellular ionic activity visualization system can manipulate biological samples based on observed and identified electro-activity. The manipulation can be adapted to provide a beneficial effect to the biological sample, hereinafter referred to as cellular activation, including but not limited to stimulation of growth or cell replication. The manipulation can also be adapted to provide destruction of certain targeted areas of the biological sample, hereinafter referred to as cellular destruction.

The cellular ionic activity visualization system can provide a method of cellular observation, cellular activation and cellular destruction, individually and in various combinations.

The cellular ionic activity visualization system can provide a method of treating disorders resulting from erratic electrical behavior of biological samples. In some embodiments, the cellular ionic activity visualization system provides a method of characterizing the electrical propagation pathways in a heart muscle in normal operation and during atrial fibrillation. In such embodiments, the location of a localized high impedance point in the electrical pathway is determined and the lower impedance pathway leading to atrial fibrillation is interrupted, by some surgical or less invasive intervention, such as but not limited to laser ablation, radio frequency (RF) cauterization or other technique, thereby reinstating the conduction cell pathway as a signal carrier once more and preventing atrial fibrillation.

There is an additional problem in vivo. Without sectioning the sample, multiple layers of cells are visible when imaged with a conventionally illuminated microscope. Confocal microscopy is an optical imaging technique for increasing optical resolution and contrast by means of adding a spatial pinhole placed at the confocal plane of the lens to eliminate out-of-focus light. It enables the reconstruction of three-dimensional structures from sets of discrete images obtained at different depths (a process known as optical sectioning) within a thick sample. A conventional microscope "sees" as far into the specimen as the light can penetrate, while a confocal microscope only "sees" images one depth level at a time. In effect, the confocal microscope achieves a controlled and highly limited depth of focus. And, it is useful for the surface layer of cells (for example myocardial cells in the cardiac example) to be visualized.

For still better depth resolution and faster image formation, two photon fluorescence imaging can be a suitable technique. There are many optical dyes suitable for in vivo use to highlight calcium, sodium and potassium concentration in cells and these can be used in some embodiments. Fluo-4 is a commonly used dye for measuring calcium ion (Ca2+) concentrations inside living cells and is often used for high-throughput screening of receptor ligands and calcium permeable ion channels.

The cellular ionic activity visualization system can provide a high-resolution determination of the ionic and thus electrical activity of a large biological sample without causing any damage to the sample. The cellular ionic activity visualization system can determine the ionic and thus electrical activity of a biological sample in vivo.

The cellular ionic activity visualization system can produce a map of electrical activity in a biological sample. The cellular ionic activity visualization system can provide a temporal map of the flow of electrical current within a biological sample.

According to a first aspect, the cellular ionic activity visualization system provides a method determining the electrical potential across a cell or plurality of cells, including: observing the electrolyte gradient within the plurality of cells.

Thus, an observation can be made of the instantaneous ionic channel activity and potential gradient across an extended biological sample. The instantaneous potential gradient across either a small sample of cells, an extended body of cells or indeed an entire organ can then be readily determined, each according to a selected observation.

In addition to determining the instantaneous electrolyte gradient it is possible to determine the changes in electrolyte gradient over time. The change in gradient with time is a proxy for electrical flow in normal healthy tissue.

In the case of the myocardium electrical impulses initiated in the sinoatrial node spreads throughout the atria through specialized internodal pathways. Loss of conduction that can occur with ischemia and infarction results in cells that do not respond to stimulus. They can be either hibernating (but not dead) or have infarcted and ultimately result in scar tissue. In either case there can be no change in intercellular ion concentration—there can be no exchange of ions between the cell and extracellular material.

If one were to observe the myocardium (or any other tissue) then these areas can appear "silent" to a visualization technique or probe as no ion flow can occur in such a region—which can be useful for multiple reasons. Firstly, such an observation can provide identification of myocardial infarction on a cellular level, which is usually preceded by a fatal mass influx of calcium. Secondly such an area can cause fatal arrhythmias and also reduces overall heart function.

It is anticipated that the system can also be useful for other areas of medicine. For example, the system can be applicable in neurology (stroke, transient ischaemic attack); oncology (tumor cell death for example in response to chemotherapy or other treatments); general tissue or wound viability assessment by many practitioners. It can be apparent to those skilled in the art that the observational technique can apply to many medical conditions.

According to a second aspect, the cellular ionic activity visualization system provides a method of determining the electrical flow through a biological sample, including: observing the temporal changes intracellular ion concentration across the sample.

The potential gradient across an extended body of cells can be determined by a wide-field observation or by a plurality of narrow-field observations of smaller groups of cells that are subsequently 'stitched' together. The system can provide a map of the instantaneous state of the electrical potential of the ensemble of cells under observation.

Furthermore, the instantaneous potential gradient across an extended body that undergoes a regular or repetitive cycle of electrical activity, such as the cardiac muscle, can be determined by sampling the plurality of narrow-field observations at substantially the same phase of the cycle.

It can be apparent to those skilled in the art that a time sequence of the instantaneous potential gradient observations can be made to provide information about the electrical signal flow in a biological sample and can furthermore be applied to a wide field investigation, such as that applied to a whole muscle, organ or entire specimen.

Thus, according to such an aspect, the cellular ionic activity visualization system provides a method determining the electrical signal flow across a cell or plurality of cells, including: observing the electrolyte gradient within the plurality of cells at a plurality of times; and determining the change in potential of each cell or region of cells (a plurality of cells) from one time period to the next; whereby the change in potential with time corresponds to an electrical signal flow.

Repetitive sampling techniques can be used to build a higher resolution time sequence than possible with simple observation. Such a technique is designed to provide very high temporal resolution by sampling a repetitive wave form (such as the repetitive beat of the cardiac muscle) across successive heart beats. such a method is analogous to the use of a strobe light to 'slow down' a high speed repetitive mechanical process. The cellular ionic activity visualization system goes further than merely selection of a suitable sample time within the myocyte cycle to infer the information.

A person skilled in the art of physiology can understand that such selection provides information about the ion concentration and inference of the electrical potential at that phase of the cycle. However electrical engineering signal processing techniques are used by the cellular ionic activity visualization system to increase the signal-to-noise ratio and sampling frequency beyond what is traditionally achievable by those of even extraordinary physiological skill.

Repetitively sampling and averaging the same point within the myocyte cycle reduces the noise floor of the measurement. Noise components are random or perhaps have some statistical distribution. Averaging a random noise component over time will reduce its influence within a 'consistent' repetitive signal.

The plurality of images is taken, each at a slightly different phase of the repetitive process and 'stitched' together to form a motion sequence. The stitching together to form a motion sequence is a technique that can be applied to the field of biological science and a sampled observation sequence collects samples (observations of the electrolyte concentration) from several successive heart beats and constructs a complete picture of the waveform from the assembled data.

Also, a low-noise measurement of the myocyte cycle can be achieved using these same signal processing techniques by phase shifting the sample point within the myocyte cycle and sequentially building up the full repetitive cycle with lower noise than achievable using conventional techniques known to those skilled in the arts of physiology and molecular biology.

It can be understood by those skilled in the art that a method described herein applies not only to a repetitive heartbeat but to any repetitive, rhythmic, peristaltic or otherwise active biological process.

Knowledge of the electrical flow in a biological sample leads to the potential for treating atrial fibrillation among other disorders. Electrical flow in the heart for example, can be overlaid onto the normal internodal conduction pathways and locations where the electrical flow departs from the normal conduction pathway can offer an insight into the onset of atrial fibrillation.

According to a third aspect, the cellular ionic activity visualization system provides a method of determining so-called high impedance points within the internodal pathways including: observation of the electrical flow within the cardiac muscle; comparison between the electrical flow and the normal internodal, or cell to cell, pathway; and location of points within the internodal, or cell to cell, pathways at which the electrical flow departs from the internodal pathway; wherein the locations of departure from the internodal, or cell to cell, pathway represent so-called high impedance points.

It can be readily apparent to those skilled in the art that location of departures of current flow from the myocardial conduction system can lead to a treatment for atrial fibrillation.

According to a fourth aspect, the cellular ionic activity visualization system provides a method of treating disorders resulting from erratic electrical behavior of biological samples, including: locating points within the electrical system which have so-called uncharacteristic localized high impedance; observing the low impedance pathway that provides conduction of the electrical signal beyond the bounds of the normal conduction system; and providing some intervention in order to render the low impedance pathway impassable for electrical signals; wherein the intervention acts to significantly increase the electrical impedance of the low impedance pathway, thereby returning the flow of electrical current to the normal conduction pathway.

The intervention is by some interventional or surgical means, such as but not limited to laser ablation, radio frequency (RF) cauterization or other technique that creates an impediment to current flow in the abnormal pathway.

In some embodiments, such a technique is applied to the conduction system of the cardiac muscle and the intervention acts to prevent atrial fibrillation and other electrically induced problems. With the cellular ionic activity visualization system whereby electrical activity is determined by observation of electrolyte gradient or electrical potential needs to be operable without causing damage to the tissue.

According to a fifth aspect, the cellular ionic activity visualization system provides a method of cellular observation, a method of cellular activation and a method of cellular destruction, each of which can be used independently or combined as selected.

The cellular ionic activity visualization system can include different applications of the core principles of the disclosure. The method of cellular observation includes applications in medical and biological screening for conditions, pathogens, rogue cells (as in cancer cells) or cellular states to name but a few of the many envisioned applications. The method of cellular observation also includes diagnostic applications, including but not limited to, arrhythmia, ischaemic, neurofibrillary tangles and immune cellular activation. The method of cellular observation includes therapeutic applications including, but not limited to, nerve signal transduction for the externalization of cell conduction to drive motor function in prosthetics.

Also, the method of cellular activation includes applications in medical and biological screening for stimulating immune cell response in infectious diseases. the method of cellular activation also includes diagnostic applications, including but not limited to, detecting the activity of osteoblasts and osteoclasts in joints and immune cell activation in oncology and hematology. Furthermore, the method of cellular activation includes therapeutic applications including, but not limited to, cellular activation distal to nerve disruption, stimulating osteoblastic activity in arthritis, stimulating components of the immune system and cellular activation for the initiation of myocardial contraction.

The method of cellular destruction includes therapeutic applications including, but not limited to, tumor destruction, destruction of bacterium and viral cells, fibrosis destruction to cease inhibition of axonal regeneration and even removal of blood waste products in renal failure patients.

According to a sixth aspect, the cellular ionic activity visualization system provides a method of determining electrical activity in a biological sample causing minimal or no damage to the sample. Furthermore, such an aspect provides a method of activation and yet still, destruction of targeted cells from within a biological sample while at the same time causing no activation or destruction of surrounding cells.

In some embodiments, the cellular ionic activity visualization system can be applied in vivo. However, the process can also be applied to biological samples of cells extracted from an organism.

In one embodiment, the method includes optical means of determining the electrolyte concentration and flow. Optical determination of electrolyte concentration uses an optical probe light source that is selectively absorbed or reflected by the electrolytes. In some embodiments, dyes or other optically active stains are applied to the biological sample and attach or otherwise associate with the selected electrolyte. These optically active stains can then be observed to indicate electrolyte concentration and hence change in concentration, or flow, with time.

According to such an aspect, the cellular ionic activity visualization system provides a method of determining ion concentration in and around a plurality of cells, including: illuminating the plurality of cells with light of a wavelength that will stimulate one or more of a plurality of ions to fluoresce; observing the plurality of cells with an optical detection system capable of imaging the plurality of cells; isolating the fluorescence of each ion species; mapping the fluorescence of each of the plurality of ion species onto the image of the plurality of cells; wherein the relative strength of the imaged intracellular and extracellular fluorescence provides a measure of the intracellular and extracellular ion concentration.

Using the system, it is possible to determine ion concentration within an extended tissue sample and to map the ion concentration onto an image of the tissue or to otherwise localize the ion concentration map within the tissue sample.

In one embodiment the optically active stains undergo excitation and fluorescence. In some embodiments, the excitation includes optical illumination at a wavelength targeted to match the absorption band of the chosen stain (or natural absorption band of the electrolyte). In such an approach, the stain attaches to the chosen electrolyte within the biological sample, the optical source causes the stain (or electrolyte) to fluoresce and the electrolyte is thereby observed. The strength of fluorescence provides an indication of the concentration of the selected electrolyte.

In some embodiments, the energy level transitions of the ionic targets are directly accessible by optical excitation or other means of excitation such that stains are not used to enable visualization of the ionic concentration within and outside the cell membrane.

Optical stimulation can be by means of broadband optical sources or narrow linewidth sources such as lasers. A high pulse rate and short pulse laser such as a mode-locked laser can be particularly suitable. Titanium Sapphire lasers can be mode-locked to produce ultra-short optical pulses. These lasers produce a train of such femtosecond pulses at frequencies of tens of megahertz.

A benefit to a mode-locked laser is the wide gain bandwidth which offers a further advantage of wide wavelength tuning range. A mode-locked laser is widely tunable and can be used to target the absorption band of the chosen optically active stain. A train of optical pulses at high frequencies also aids in the ability to reduce 'noise' in the measurement—the biological process is effectively steady state over the course of many optical pulses. This can allow multiple images or measurements to be acquired and processed using the signal processing methods disclosed in the second aspect.

There is a significant complication with optical illumination or stimulation of a biological sample. From an optical perspective, biological samples can be considered to be an aggregation of scattering centers. Each cell is weakly absorbing at the chosen illumination wavelength and the optical source penetrates a significant depth into the sample. This can mean that many overlapping layers of cells are illuminated. Even if a cell is illuminated and its electrolyte concentration can be clearly determined in isolation, many layers of randomly organized such cells will be illuminated to varying degrees and the resulting fluorescence (or optical return signal) of many overlapping cells will make it impossible to make any clear determination of electrolyte concentration (with or without an optically active stain).

In some embodiments, the cellular ionic activity visualization system includes a method of optically imaging only a thin layer of cells. Confocal microscopy is an optical imaging technique for increasing optical resolution and contrast of a micrograph by means of adding a spatial pinhole placed at the confocal plane of the lens to eliminate out-of-focus light. It enables the reconstruction of three-dimensional structures from sets of images obtained at different depths (a process known as optical sectioning) within a thick object. A conventional microscope "sees" as far into the specimen as the light can penetrate, while a confocal microscope only "sees" images one depth level at a time. In effect, the method achieves a controlled and highly limited depth of focus. Most frequently the system employs a laser scanning optical source.

According to such an aspect, the cellular ionic activity visualization system provides a method of determining ion concentration in and around a thin layer containing plurality of cells, including: illuminating the plurality of cells with light of a wavelength that will stimulate one or more of a plurality of ions to fluoresce; observing the plurality of cells with an optical detection system capable of selectively imaging light emitted from a thin layer containing the plurality of cells; isolating the fluorescence of each ion species; mapping the fluorescence of each of the plurality of ion species onto the image of the plurality of cells; wherein the relative strength of the imaged intracellular and extracellular fluorescence provides a measure of the intracellular and extracellular ion concentration within the thin layer.

In some embodiments, two-photon excitation allows imaging of living tissue up to about one millimeter in depth. It differs from traditional fluorescence microscopy as the wavelengths of the two exciting photons are longer than the wavelength of the resulting emitted light. Longer wavelengths minimize scattering in the tissue and the background signal is strongly suppressed. Both effects lead to an increased penetration depth for these microscopes. Two-photon excitation microscopy typically uses near-infrared excitation light, such as that generated by the mode-locked Titanium Sapphire laser, to excite the optically active stain.

In some embodiments of the cellular ionic activity visualization system, a laser system provides the illumination source for mapping electrical flow and the 'surgical' technique for localized intervention via laser ablation (or cauterization), creating a localized high-impedance pathway where the short circuit otherwise occurred.

A study of genetically modified zebra fish to observe its cardiac ion channels is known. While a useful laboratory technique it may not be suitable for use as a human clinical tool. The authors of this study are skilled in the arts of optical physics, chemistry and microbiology applying their art to a study of the effect of developmental stages on the ion currents of a zebrafish using a novel optical detection method. The authors are skilled in the art of scientific methods directed to extending fundamental knowledge about physiological processes on a cellular level. Someone of ordinary or even extraordinary skill in the art of optical physics, chemistry or microbiology may not possess sufficient skill in the art of cardiology or surgery to apply these techniques to effect treatment of cardiological disorders by observation or selective destruction of a targeted cell group.

Such embodiments employ an electrical current flow visualization system for mapping the current flow of the tissue, such as in vivo, computer system for calculating the position of the short circuit and determining the optimum location of the intervention site before controlling the intervention cycle and treatment system for increasing the electrical impedance of the short circuit path.

In yet another embodiment of the cellular ionic activity visualization system, illumination is provided at an oblique angle to the surface of the tissue. Where forward scattering is dominant, which limits penetration depth of the illumination wavelength and can allow a reduced the depth of field condition in the detection system.

In some embodiments, multiple optical sources are employed to determine the time dependence of the ion transport process, whereby each optical source is adapted to enable visualization of a different ion species and visualization is employed by any of the methods taught in the cellular ionic activity visualization system.

In some embodiments of targeted activation or destruction of cells, energy is deposited in the targeted cells via application of optical energy whereby the optical energy is absorbed via a stain attached to the targeted cells. In another embodiment, energy is deposited in the targeted cells via a variety of means including but not limited to, x-ray, ultrasound, magnetic resonance excitation and the like.

In yet another embodiment ion channel mapping is conducted using a fiber optic based light delivery and imaging system. Such a system can employ a range of imaging techniques but in some embodiments a gradient index lens it attached to the distal end of a fiber optic light delivery cable. Light emanating from the core of the fiber can be focused by the gradient index lens onto or into the biological sample. Such light can be scattered around but there can be a specific depth within the biological sample from which light scattered can be imaged back onto the core of the optical fiber to propagate back toward the light source.

A fiber optic delivery system allows illumination and optical imaging via remote access, which can be achieved, but limited to, through a scoped surgical device or indeed through an intravenous cannula enabling access to the vascular system and, thus, organs. The term laparoscopic refers to a scope used in the abdomen. Thoracoscopic refers to a scope used in the thorax. References to laparoscope, thoracoscope, endoscope and the generic term scope are interchangeable in this disclosure and are equally interchangeable with the terms 'keyhole surgical device' or 'minimally invasive surgical device' as applicable. In the example case of an internal myocardial inspection, the device can be delivered via cannula into the atria to undertake an internal survey of the ion channel activity and subsequently to an understanding of branch points in atrial fibrillation and total cardiac conduction circuits.

In such embodiments, a fiber optic endoscope can need to be employed in the confocal arrangement to allow thin sections to be imaged. Furthermore, according to such an aspect, the cellular ionic activity visualization system provides a method of determining ion channel activity in a plurality of cells, including: observing a plurality of cells at a plurality of times; determining the intracellular and extracellular concentration of each of a plurality of ion species at the plurality of times; determining the changes in relative intra and extracellular ion concentrations for each of the plurality of ion species.

It can be apparent to those skilled in the art that one can merely need to know the relative concentrations of the ion species at the plurality of times.

According to the aspect, the cellular ionic activity visualization system provides a method of determining ion concentration in and around a plurality of cells, including: delivering an illumination source to a first end of a fiber optic cable; illuminating a field containing the plurality of cells with light of a wavelength that will stimulate one or more of a plurality of ions to fluoresce from a second end of the fiber optic cable; capturing light emitted by the plurality of ions by an optical system with a narrow depth of field and transmitting the captured light into the second end of the fiber optic cable; relaying the light emitted by the first end of the fiber optic cable to a detection system; selectively measuring and recording the light emitted from each of the plurality of ions within the field; wherein the intensity distribution of light across the field provides a map of the concentration of each of the plurality of ion species.

In some embodiments, the fiber optic cable can have one or many cores. Where a plurality of cores is contained within the fiber optic cable each core of the proximal the first end can be sequentially illuminated by the illumination source or substantially all of the plurality of cores can be simultaneously illuminated.

In some embodiments, the field of illumination is illuminated with a uniform intensity of light. In another embodiment, the field is illuminated with a known intensity profile such that the known intensity profile can be used to compensate for the intensity distribution of the measured intensity across the field.

Using the mechanisms disclosed herein, it is possible to determine ion concentration within an extended tissue sample and to map the ion concentration onto an image of the tissue or to otherwise localize the ion concentration map within the tissue sample.

In some embodiments, a graded index (GRIN) lens is employed at the distal or the second end of the fiber optic cable as a means of focusing the illumination source into the field and for capturing the emitted light for transmission into the distal the second end of the fiber optic cable.

Optical pattern recognition techniques can also be able to determine whether fluorescence was emanating from an array of point sources within the image field (from within cells) or from extended filamentary areas representing interstitial areas exterior to the cells. It can be readily apparent to those skilled in the art that the relative intensity of light from intracellular and extracellular locations can provide a measure of the ion channel activity.

According to such an aspect, the cellular ionic activity visualization system provides a method of determining the concentration of a plurality of ion species in and around a plurality of cells, including: exciting at least one ion species to fluoresce; capturing an image of the fluorescence produced by the excitation of the one or more ion species; filtering the image to isolate the fluorescence of each of the plurality of ion species; designing an optimum pattern recognition function for the specific plurality of cells; applying the pattern recognition function to each of the plurality of filtered images to provide a plurality of output images each of which corresponds to a respective filtered image; wherein each of the output images provide an indication of whether the respective the filtered image matches the fluorescence pattern for a given ion species concentration distribution.

According to such an aspect, the cellular ionic activity visualization system provides a method of determining ion channel activity in a plurality of cells, including: exciting at least one ion species to fluoresce at a plurality of times; capturing an image of the fluorescence produced by the excitation of the one or more ion species at each of the plurality of times; filtering each of the images to isolate the fluorescence of each of the plurality of ion species at each of the plurality of times; designing an optimum pattern recognition function for the specific plurality of cells; applying the pattern recognition function to each of the plurality of filtered images to provide a plurality of output images each of which corresponds to a respective filtered image at a respective time and represents the concentration map of each of the ion species at each of the plurality of times; determining the difference between the concentration map of each of the ion species at substantially each sequential time of the plurality of times; wherein the time sequence of the concentration maps of each of the plurality of ions indicates the flow of each of the ion species within the field of view.

In some embodiments, the excitation is via optical stimulation. In one embodiment, the cellular ionic activity visualization system provides for the application of ion specific dyes. In another embodiment, the excitation is via another form of electromagnetic stimulation.

The cellular ionic activity visualization system can include methods and apparatus for the imaging of a narrow field of view and hence a thin layer of cells. This is typically done by observing a thin layer of cells perpendicular to the direction of propagation of the illumination source. However, the cellular ionic activity visualization system also can include a method of determining the ion concentration and hence ion channel activity in a thin layer along the direction of propagation. This is achieved by sequentially shifting the confocal depth into the plurality of cells under investigation while only measuring light emitted on a given axis perpendicular to the direction of propagation.

The methods taught rely on access to the surface of an organ or group of cells to be mapped. It is preferable in some circumstances to sample the interior surface of a hollow cellular body. One such example is the heart. Access can be more readily available to the interior surface of the myocardium via endovascular access, than the exterior surface. It is preferable in some circumstances to provide a means to map the electrical activity of the interior of the heart. Other organs, such as the hollow viscera of the gastro-intestinal system can also be more readily accessed via methods of endoscopy.

According to a seventh aspect the cellular ionic activity visualization system provides a method of determining flow of ions into and out of a plurality of cells and hence the ion channel activity using an enclosed volume sampling technique. In some embodiments, the probe employs an electrochemical sensor. Using a plurality of sensors that are tuned to different ion species it is possible to measure the concentration of a plurality of ion species in an enclosed volume adjacent the plurality of cells.

According to an eighth aspect, the cellular ionic activity visualization system provides a method of determining ion channel activity in a plurality of cells, including: creating an enclosed volume adjacent to the plurality of cells; waiting for a period of time to enable the ion concentration within the enclosed volume to reach equilibrium; monitoring the ion concentration over a period of time; wherein an increase in ion concentration within the enclosed volume is a direct measure ion flow out of the cell's ion channel.

In some embodiments, the volume of the enclosed chamber is chosen to provide the greatest sensitivity and dynamic range for the chosen ion sensor.

If the enclosed volume is small enough to encircle the ion channels of only one cell, then the technique can be employed to determine the ion channel activity of a cell.

Optical determination of electrolyte concentration uses an optical probe light source that is selectively absorbed or reflected by the electrolytes. In some embodiments, dyes or other optically active stains are applied to the biological sample and attach or bind with selected ions.

According to a ninth aspect, the cellular ionic activity visualization system provides a method of visualization and treatment in neurological medicine and research. A neuron or nerve cell is an electrically excitable cell that processes and transmits information through electrical and chemical signals. These signals between neurons occur via specialized connections called synapses. Neurons can connect to each other to form neural networks. Neurons are major components of the central nervous system, including the brain and spinal cord, and of the peripheral nervous system, including the autonomic ganglia as well as sensor and motor neurons.

There are several types of specialized neurons. Sensory neurons respond to stimuli such as touch, sound or light and other stimuli affecting the cells of the sensory organs that then send signals to the spinal cord and brain—inputs to the brain. Motor neurons receive signals from the brain and spinal cord to enact functions, exemplified by, but not limited to, muscle contractions and affect glandular function—outputs from the brain. Interneurons connect neurons to other neurons within the same region of the brain, or spinal cord in neural networks. Neurons as discussed in the cellular ionic activity visualization system, include peripheral and central nervous systems, wherein spinal or cerebral neurons can exhibit ion channel patterns and sequences providing insights into higher mental function.

Neurons are electrically excitable, maintaining voltage gradients across their membranes by means of metabolically driven ion pumps in much the same way as the cardio myocyte responds to ion concentration. Ion channels embedded in the membrane generate intracellular-versus-extracellular ions potentials. Neural function can depend on the synaptic signaling process, which is partly electrical and partly chemical. The electrical aspect depends on properties of the neuron's membrane. These include ion channels that permit electrically charged ions to flow across the membrane, and ion pumps that actively transport ions from one side of the membrane to the other. Most ion channels are permeable only to specific types of ions. Some ion channels are voltage gated, meaning that they can be switched between open and closed states by altering the voltage difference across the membrane. Others are chemically gated, meaning that they can be switched between open and closed states by interactions with chemicals that diffuse through the extracellular fluid. If the voltage changes by a large enough amount, an all-or-none electrochemical pulse called an action potential is generated, which travels rapidly along the cell's axon, and activates synaptic connections with other cells.

Neurological conditions can result from an interruption in the normal electro-chemical process in a nerve cell. Examples include Epilepsy and motor neuron diseases such as Parkinson's disease, Amyotrophic Lateral Sclerosis (ALS) and Multiple Sclerosis.

In one embodiment, the cellular ionic activity visualization system provides a method of determining the electrical activity associated with neurological activity. In a particular embodiment, the cellular ionic activity visualization system provides a method of determining the location of a given electro-chemical irregularity in a neuron. Furthermore, the cellular ionic activity visualization system provides a method of stimulating the neuron to correct the electro-chemical irregularity. In some embodiments, the cellular ionic activity visualization system provides a method of providing targeted destruction of particular sections of a neuron.

In a tenth aspect the cellular ionic activity visualization system provides an apparatus for delivery of a plurality of ion channel sampling devices. In some embodiments, the system provides a two dimensional array of ion sampling devices with enough mechanical compliance to be able to firstly contract within a small delivery device (such as but not limited to a cannula or a laparoscopic device) and secondly confirm to the three dimensional surface of a biological sample.

According to an eleventh aspect, the cellular ionic activity visualization system provides a method of determining ion channel activity in a plurality of cells, including: creating an enclosed volume adjacent to the plurality of cells; waiting for a period of time to enable the ion concentration within the enclosed volume to reach equilibrium; monitoring the ion concentration over a period of time; wherein an increase in ion concentration within the enclosed volume is a direct measure ion flow out of the cell's ion channel.

According to a twelfth aspect, the cellular ionic activity visualization system provides a method of mapping the electrical signal flow through a biological sample including: sampling the electrical potential of each of a plurality of substantially adjacent cell membranes at a plurality of measurement points at substantially the same first time; determining the potential gradient across the plurality of cells at the first time; sampling the electrical potential of each of a plurality of substantially adjacent cell membranes at substantially the same plurality of measurement points at substantially the same second time; comparing the electrical potential at each of the plurality of measurement points at the first and second times; determining a net change in potential across the plurality of measurement points between first and second times; calculating the net current flow between each of the plurality of measurement points.

According to such an aspect the cellular ionic activity visualization system provides an apparatus for measuring the change in cellular membrane potential as an electrical signal passes through a biological tissue sample.

In some embodiments, the spacing between adjacent measurement points is substantially smaller than the diameter of the cell under investigation such that there are many measurements across each cell. With high enough temporal resolution between samples occurring at the first and second times, the wavefront of the potential change passing through each cell can be observed. It is furthermore advantageous to have multiple measurements across a given cell because it allows averaging of measurements to improve the accuracy given a suitable measurement time constant.

In yet another embodiment, the spacing between adjacent measurement points is substantially the same as the diameter of the cell under investigation.

In some embodiments, the measurement points are part of a substrate. Furthermore, the measurement points can be implemented as electrically insulating islands with an electrically conductive measurement point sitting proud of the surface of the substrate.

In another embodiment, the measurement face of the substrate can be substantially flat with each conductive measurement point exposed to the biological sample only through windows or voids in a thin electrically insulating mask. In another embodiment, the mask can be of substantial thickness such that when applied to the biological sample the volume enclosed by the void in the mask is of a predefined volume suitably for use with a chemical sensor rather than an electrically conductive sensor according to a seventh aspect of the cellular ionic activity visualization system. In yet a further embodiment, the mask can be thickened in a region surrounding the voids providing a positive pressure seal against the cell wall.

It should further be noted across the spectrum of embodiments that allow identification of particular cellular types or components the method can include a tuning of the energy frequency to subsequently stimulate cells, such as through the delivery of energy to nervous or muscle tissue that lowers the conduction threshold sufficiently to enable depolarization thus initiating cellular activation—which can be achieved through a single or plurality of lasers or via other means such as, but not limited to, electromagnetic stimulation that are targeted to stimulate ion channel action thereby pumping ions into our out of a given target cell.

One of the core aims of the cellular ionic activity visualization system is to determine the electrical current flow through biological materials and in particular the flow of current associated with sinus rhythm in myocardial tissue. A number of methods and apparatus have been disclosed ranging from optical through biochemical and even galvanic electrical measurement. Electrical current induces a magnetic field surrounding the conductor and the magnetic field can be measured in order to determine the electrical current flow. It is possible to determine the electrical signal flow through a biological sample by measuring the magnetic field induced by the current flow.

Atomic transitions can be particularly sensitive when the magnetic response of the spins is measured optically—which utilizes energy-level transitions that are accessible from the ground state in paramagnetic atoms and are coupled to optical transitions. In this case, optical fields can be used to polarize the sensing atoms (via optical pumping) and for detection (via change in the absorption or fluorescence signal induced by spin resonance). One such structure that exhibits the phenomenon is the Nitrogen-Vacancy defect (NV center) in diamond-like carbon lattices. There are many of the so-called color centers in diamond, but the NV center is particularly suitable.

Although several materials allow optical spin readout, diamond has particular advantages. Spins in diamond are very well isolated from lattice phonons and the coherence time of diamond color centers (which is directly related to the sensitivity of magnetometers) is long, even under ambient conditions.

According to a thirteenth aspect, the cellular ionic activity visualization system provides a method of and apparatus for determining the electrical flow in a biological sample using optical probing of the magnetically sensitive spin NV center in diamond.

According to the method, the cellular ionic activity visualization system can include an apparatus for measuring the electrical flow including: an optical source for illuminating a first proximal end of a fiber optic cable; a diamond sample containing at least one NV center attached to a second distal end of the fiber optic cable; an optical detection system for detecting the light transmitted from the second distal end of the fiber optic cable and subsequently emitted from the first proximal end of the fiber optic cable; wherein light detected by the optical detection system provides a measure of the magnetic field in the vicinity of the diamond sample.

In some embodiments, the diamond sample also includes an optical cavity which creates an increased optical intensity in the region of the NV centers thereby increasing the sensitivity of the measurement system.

In some embodiments, the cellular ionic activity visualization system can be used to determine electrical signal flow in biological samples.

It should be noted that the various features of each of the above aspects of the system can and are intended to be combined as suitable and desired.

Furthermore, it should be noted that the system also provides apparatuses and systems arranged to perform each of the methods of the system described above.

Furthermore, the system envisages utilizing a plurality of lasers, optical sources or even broadband sources to determine the activity of multiple ions channels concurrently.

The cellular ionic activity visualization system is intended to be combined with other techniques that allow visualization of other biological parameters, hereinafter referred to as non-ionic visualization. In one such embodiment, the ion channel information is combined with an optical absorption profile of the sample which provides information about concentrations of other components. In another embodiment, ion channel information is combined with information obtained from conventional medical imaging techniques such as, but not limited to, x-ray, ultrasound, magnetic resonance imaging (MRI), computer assisted tomography (CAT) scans, positron emission tomography (PET) scans and the like. Indeed, the non-ionic visualization can include acoustic, radiofrequency (RF) or other excitation techniques.

Another embodiment of the cellular ionic activity visualization system employs the temporal evolution of the ionic and non-ionic visualization techniques to determine movement of or within the biological sample or even the evolution of a given state of the sample.

It will be readily appreciated by those skilled in the art that non-optical means can be employed to determine concentrations of other components of the biological sample in parallel with the ion channel visualization techniques of the cellular ionic activity visualization system and combinations therein are anticipated by the cellular ionic activity visualization system.

In addition, apparatuses according to the system can be embodied in various ways. For example, such devices could be constructed in the form of multiple components on a printed circuit or printed wiring board, on a ceramic substrate or at the semiconductor level, that is, as a silicon (or other semiconductor material) chip. Optical devices can similarly be constructed in the form of multiple components, monolithic devices or combinations of both and be used in conjunction with other surgical tools.

Although much of the discussion of the system is centered on the cardiac system and methods, systems and apparatus for determining the electrical flow in the cardiac muscle, the techniques of the cellular ionic activity visualization system apply to biological samples which use ion transfer as a mechanism for ion channel visualization or electrical signal flow and accordingly are intended to be used therein.

Furthermore, the methods taught to treat atrial fibrillation are intended to be used to treat a variety of conditions resulting from abnormal electrical activity of the heart or any other biological sample. Also, treatment options are anticipated for the cellular ionic activity visualization system beyond the realm of cardiology.

The human heart 10 shown schematically in a frontal cross-sectional view in FIG. 1 includes four chambers, the right atrium 12, the right ventricle 14, the left atrium 16 and the left ventricle 18. The sinoatrial node 20 is the heart's pacemaker and sets the rhythm of the heart with the signal propagation to the atrioventricular node 22 via the internodal pathways 24 as well as across to the left atrium via pathway 26. The signal propagates from the atrioventricular node 22 to the ventricles via the Purkinje fiber system pathway 28. Additionally, conduction is spread throughout the heart with cell to cell communication via gap junctions.

This impulse, initiated in the sinoatrial node 20, spreads throughout the atria through specialized internodal pathways. The internodal pathways include three bands (anterior, middle, and posterior) that lead directly from the SA node to the next node in the conduction system, the atrioventricular node 22. The impulse takes approximately 50 ms (milliseconds) to travel between these two nodes. As the impulse reaches the atrioventricular septum, the connective tissue of the cardiac skeleton prevents the impulse from spreading into the myocardial cells in the ventricles except at the atrioventricular node—which allows the signal to follow the Purkinje fiber system pathway 28 and initiate ventricular contraction throughout the heart.

Figure 2:
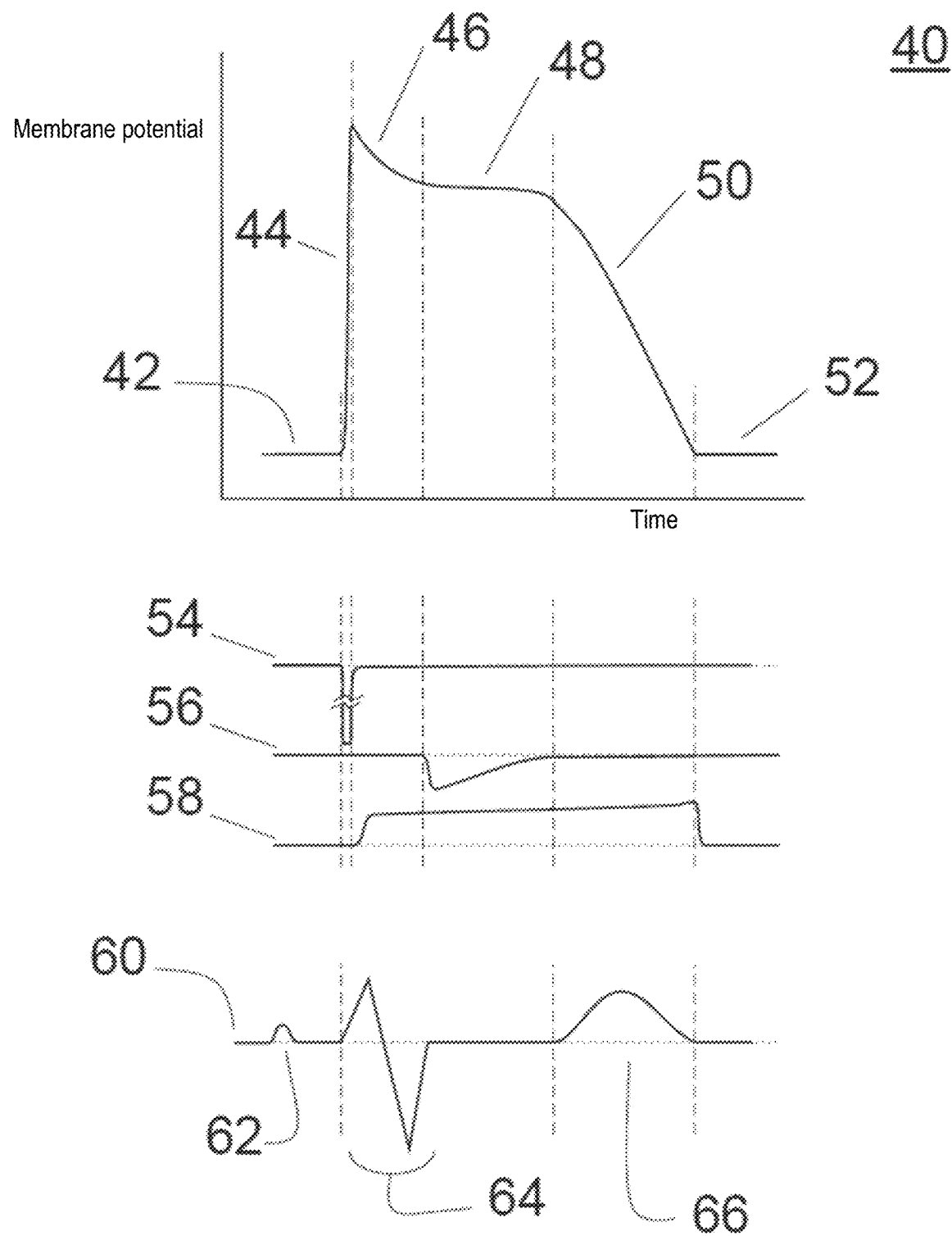
FIG. 2 shows schematic representations of the myocardial contractile cell membrane potential and the relationship between ion pathways and potential.

The myocardial cell membrane potential 40 is shown schematically in FIG. 2. Phase 4 is shown at graph portion 42, the 'steady-state' pre-pulse condition, where potassium channels are open to regulate membrane potential. Phase 0 is shown at graph portion 44 where massive sodium ion flows occur and potential changes within a few milliseconds. Phase 1 is shown at graph portion 46, phase 2 at graph portion 48, phase 3 at graph portion 50 and phase 4 at graph portion 52. Sodium ion concentration (from the phase 4 steady state level) is shown at graph portion 54, calcium ion concentration at graph portion 56 and potassium ion concentration at graph portion 58. By convention, inward cellular currents of ions are represented by a downward inflection and outward with an upward inflection.

The electrocardiogram (ECG) trace is furthermore show at graph portion 60. The various phases of the ECG trace are labelled as shown, with P wave phase shown at graph portion 62, the compound QRS complex phases are shown together at graph portion 64 and the T wave phase is shown at graph portion 66.

Figure 3:
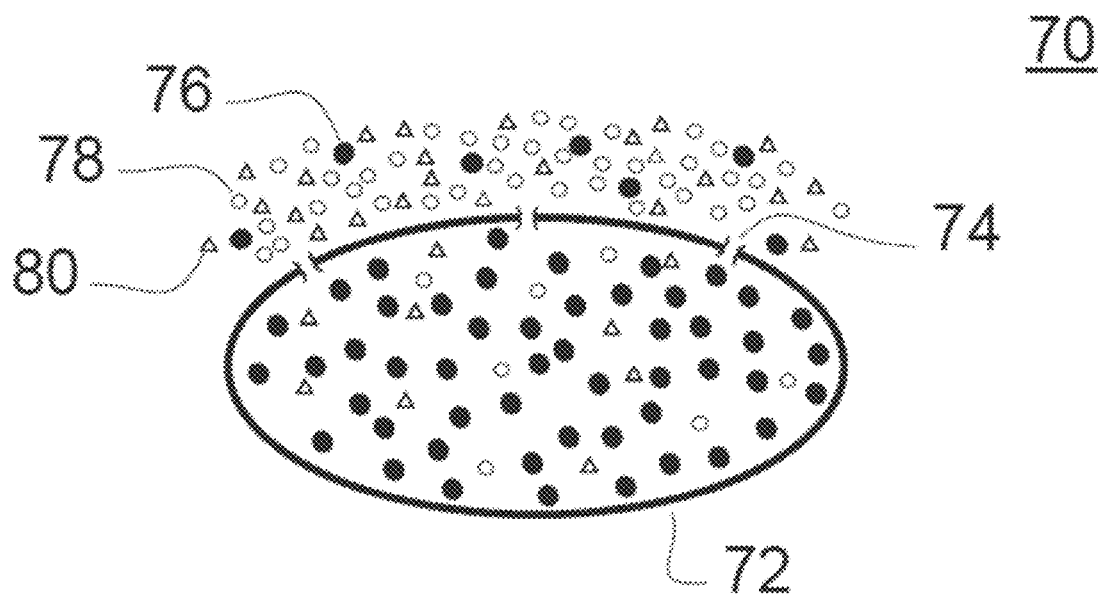
FIG. 3 illustrates a schematic representation of the ion concentration across a cardiac myocyte.

The myocardial cell membrane potential is defined by the flow of ions across the cell wall. A myocardial contractile cell 70 is shown schematically in FIG. 3. The cell membrane 72 contains various pathways for the flow of ions, such as the shown three pathways 74, one each for calcium ions 76, potassium ions 78 and sodium ions 80. The case depicted in the schematic shows a high concentration of sodium ions within the cell compared to the extracellular concentration. High internal sodium ion concentration, shown at graph portion 54 in FIG. 2, is coincident with the initiation of the QRS ECG phase, 64. As the myocyte contraction cycle continues electrolyte concentration changes and the myocyte potential changes accordingly. The change in ion concentration is reflected in the cell potential, the change of which and that of its neighbors results in electrical flow across the cardiac muscle. It is an observation of change in ion concentration with time that can lead us to an understanding of electrical current flow.

The cellular ionic activity visualization system's three defined objectives, cellular observation, cellular activation and cellular destruction can be used for research, screening and diagnostic purposes, hereinafter referred to as diagnostic applications and therapeutic applications.

In addition to general muscle mapping, the cardiac applications can include, but are not limited to, cardiac muscle mapping, cardiac arrhythmia detection and ischemia detection, and diagnostic applications. In a cardiac sense, cellular activation includes, but is not limited to, initiation of myocardial contraction (a therapeutic application) and cellular destruction includes, but is not limited to, fibrosis destruction in arrhythmia treatment, atherosclerotic plaque destruction and scar tissue manipulation (therapeutic applications).

Figure 4:
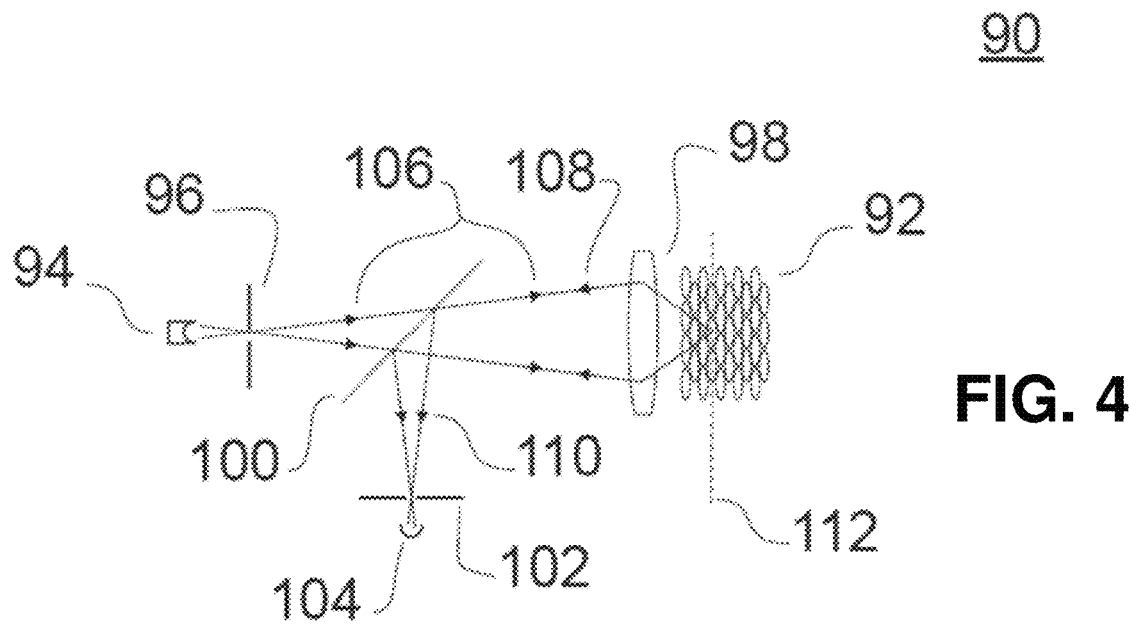
FIG. 4 illustrates a schematic representation of an optical system for determining the concentration of various ions within a biological sample, in accordance with some embodiments of the present disclosure.

FIG. 4 shows a schematic representation of an optical means 90, such as a microscope, for observing ion concentration. A confocal microscope is shown with the optical means 90 for observing, in this case, a biological tissue sample. The optical means 90 includes an optical source 94, a pinhole aperture 96 a focusing element 98, a beam splitter 100, an output pinhole aperture 102 and an optical detector 104. The optical source 94 can be a broadband light source such as an incandescent globe, a narrowband source such as a laser including a tunable laser or other optical source. The optical focusing means can be a lens, mirror element or other means of simple or compound types. The beam splitter 100 can be a partially reflecting mirror, a mirror with a wavelength dependent reflectivity profile, a polarization dependent beam splitter (in which case a set of polarization determining and polarization changing optics can also be included) or any other beam splitting means.

Light from the optical source 94 passes through a pinhole aperture and propagates (e.g., a forward propagating beam 106) through beam splitter 100 before being focused by focusing element 98 onto the tissue sample 92. Light can scatter from the tissue sample 92 and rays from the scattering which can propagate backwards (e.g., a backwards propagating beam 108) along the optical axis formed by the forward propagating beam 106, are reflected off the beam splitter 100 and form an image of the tissue sample 92 at the output pinhole aperture 102 and those rays which pass through output pinhole aperture 102 are collected by the optical detector 104. It is a property of such an arranged optical system that only light that emanates from a small region of the tissue sample 92 will pass through the output pinhole aperture 102. The system forms a highly discriminating optical filter that rejects light from either in front of or behind the focal plane 112 of the optical system.

Figure 5:
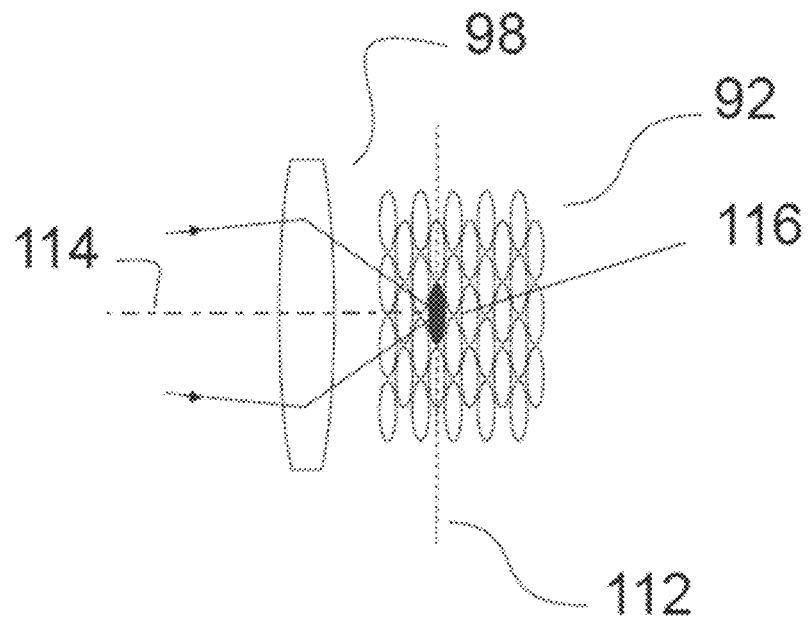
FIG. 5 illustrates an expanded section of FIG. 4 with additional detail shown, in accordance with some embodiments of the present disclosure.

Furthermore, light emanating from the focal plane 112 is also rejected by the output pinhole aperture 102 if it is displaced laterally from the optical axis 114 of the optical system, as shown in FIG. 5. This means that the detectors only 'sees' light emanating from a point on the optical axis 114 of the optical system and at a depth equal to the focal plane 112. The system only 'sees' light emanating from the focal point 116. Also, the system can visually target a cell or group of cells at a predefined depth within the tissue and have a very short depth of focus but eliminate emissions from neighboring cells. The aforesaid can overcome the problems associated with scattered light from nearby cells clouding the image.

Also, a system that scans the output pinhole aperture 102 laterally in its image plane can image a layer of cells at a fixed depth in the sample.

The cellular ionic activity visualization system is applicable to many other branches of medicine and biological study—which can include, without limitation, bacterial analysis and manipulation, gastroenterology, rheumatology, oncology, immunotherapy, renal medicine and hematology.

Figure 6:
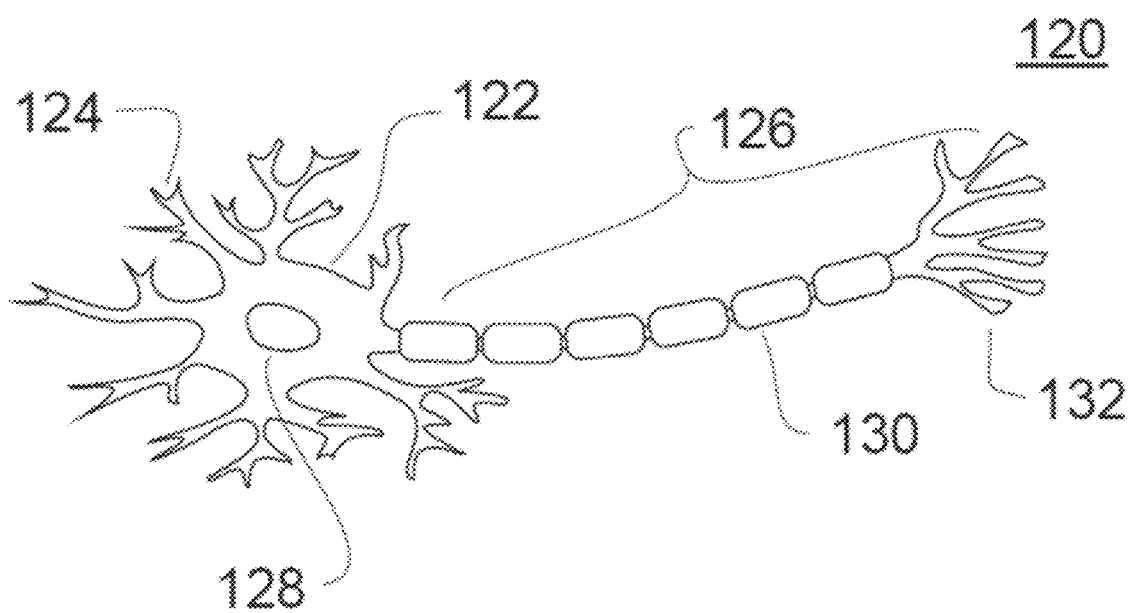
FIG. 6 illustrates a schematic representation of a generalized neuron.

A typical neuron 120 is shown in FIG. 6. Such a neuron can include a cell body or soma 122, dendrites 124 and an axon 126, with the soma 122 containing the cell nucleus 128. Dendrites are thin structures that arise from the cell body branching multiple times, giving rise to dendrites 124. The axon 126 (often called a nerve fiber) is covered in a segmented myelin sheath 130 can stretch as far as 1 m in humans and is terminated in a smaller axon terminal 'tree' 132.

Nerve fibers are often bundled into fascicles and in the peripheral nervous system bundles of fascicles make up nerves (like strands of wire make up cables). At the majority of synapses, signals are sent from the axon terminal 132 of one neuron to dendrites of another neuron.

Neurons, or nerve fibers, can be damaged by physical trauma and neurological diseases. Manipulation of the ion transport function offer the potential for a suitable treatment protocol via providing guidance for the growth pathway.

It is preferable in some circumstances to sample the interior surface of a hollow cellular body. One such example is the heart. Access is more readily available to the interior surface of the myocardium than the exterior surface. Access to the exterior surface is via a traumatic operation in which the chest cavity is opened while the interior surface is accessible via a cannula that enables a probe to travel from say the femoral artery into the heart. It is preferable in some circumstances to provide a means to map the electrical activity of the interior of the heart, or both concurrently.

Figure 7:
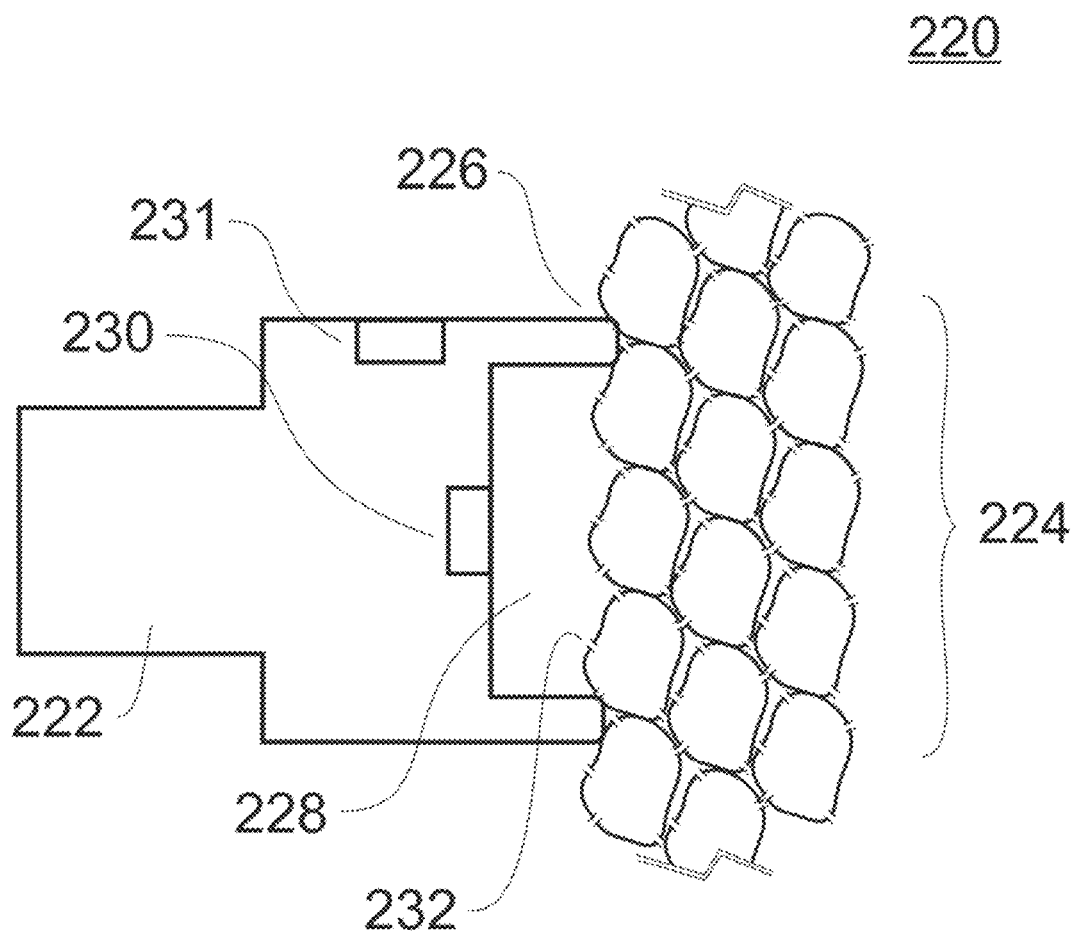
FIG. 7 illustrates a schematic representation of an ion sampling apparatus, in accordance with some embodiments of the present disclosure.

While a system can be achieved using optical means with fiber-optical based devices, other devices can be more practical in some circumstances. FIG. 7 shows a schematic representation of an electrochemical probe 220 according to the cellular ionic activity visualization system. Electrochemical probe 222 is used to determine the ion channel activity of a plurality of cells 224. Electrochemical probe 222 is placed in contact with the plurality of cells 224 such that the tip of the probe 226 makes a physical seal against the cells. This creates an enclosed chamber 228 which can monitor ion concentration via ion sensor 230. A second ion sensor 231 can monitor the ion concentration in the bulk medium (e.g., blood) outside of the enclosed chamber 228.

Ions flow in and out of the cells through ion channels 232 as the cells go through their ion exchange cycle. The concentration of ions within the enclosed chamber 228 will reach equilibrium because there will be no exchange of the contents of the enclosed chamber 228 with the medium surrounding the probe. With an appropriate selection of the volume of the enclosed chamber 228 the variations in ion concentration will be matched to the sensitivity of the ion sensor 230, which is in stark comparison to a probe measuring ion concentration of the bulk medium, for example within the chamber of the heart. In some embodiments there may additionally be a second ion sensor 231 that measures the ion concentration in the bulk medium. In such an embodiment a difference measurement circuit may be used to increase the sensitivity of the detector. The difference measurement circuit compares ion sensors 230 and 231 with the resulting signal representing only the difference in ion concentration. This removes the background ion concentration (DC component of the signal) and allows greater measurement resolution.

Figure 8:
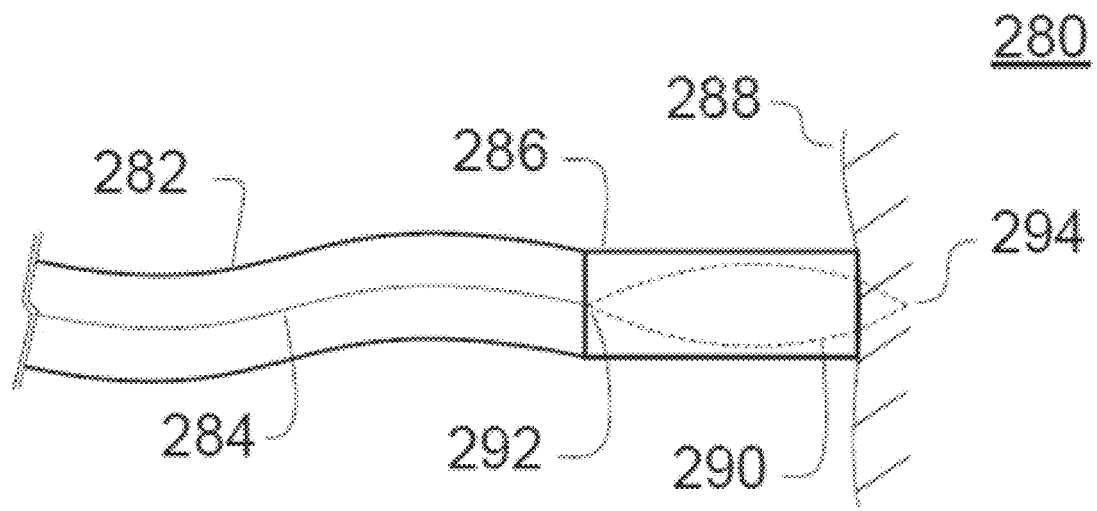
FIG. 8 illustrates a schematic representation of a graded index lens focusing mechanism used for fiber optic delivery and imaging, in accordance with some embodiments of the present disclosure.

In another embodiment, a fiber optic delivery system 280 is shown schematically in FIG. 8 that provides the ion channel activity measurement. Fiber optic cable 282 has a core 284 which carries light to a graded index lens 286 which is brought into contact with tissue 288. The optical ray 290 emanating from the end 292 of the core 284 of the fiber optical cable bundle 282 is focused at area 294 in the biological sample.

The graded (or gradient) index lens 286 can be adapted to produce an image of end 292 at the gradient index lens and biological sample interface or within the bulk volume of the biological sample. The useful point to note with this is that the small core of the optical fiber acts as a spatial filter to the backscattered light from the biological sample thereby selecting light from a given narrow depth of field plane within the biological sample. The depth of the focus of area 294 within the tissue 288 can be controlled by the parameters of the graded index lens. A combination of the graded index profile and length of the lens will determine the depth of focus within the tissue 288 and also the theoretically achievable spot size at the focus of area 294.

Figure 9:
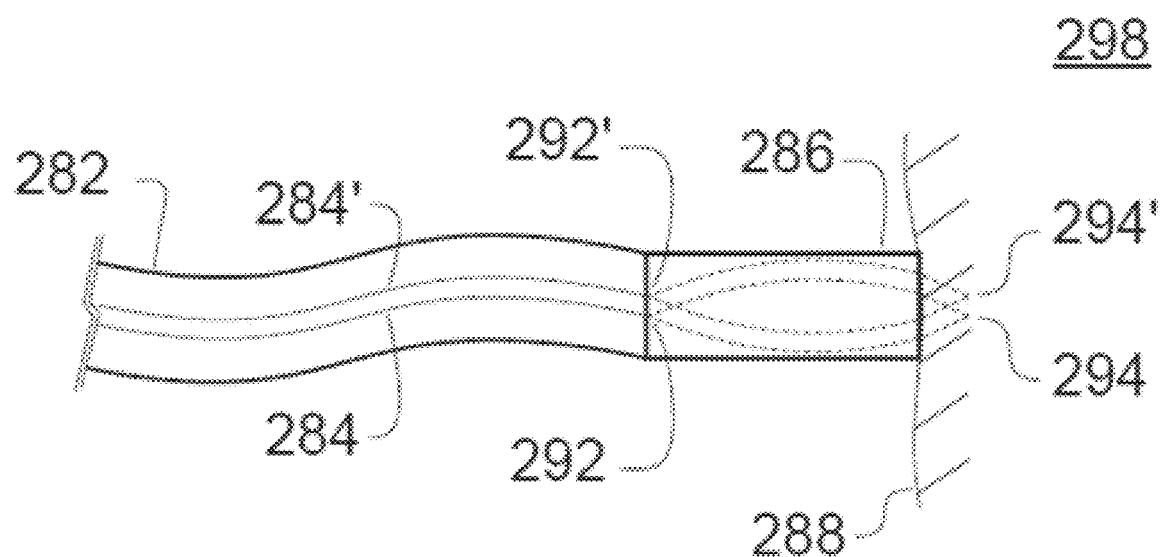
FIG. 9 illustrates a schematic representation of a graded index lens focusing mechanism used for fiber optic cable carrying two fiber optic cores, in accordance with some embodiments of the present disclosure.

In another embodiment, the fiber optic delivery cable includes a plurality of fiber optic cores bundled together. FIG. 9 is a schematic representation of the optical rays emanating from two cores (representative of any number of cores in a cable carrying a plurality of cores) into a graded index focusing element 298 (which is representative of any focusing element) where similar numbering has been adopted from FIG. 8 for similar items. It should be noted that any focusing element can be used here, including without limitation a conventional optical lens or plurality of lenses. Fiber optical cable bundle 282 contains two fibers or cores 284 and 284' graded index lens 286 and tissue 288 under investigation. The interface between the lens 286 and the cores 284 and 284' are shown as ends 292 and 292' respectively. Index lens 286 creates an image of the tissue at areas 294 and 294' at ends 292 and 292' respectively. The small diameter of the core 284 of the optical fiber provides spatial discrimination within the sample similar to that of aperture 102 of FIG. 4, particularly when used in a confocal arrangement.

Figure 10:
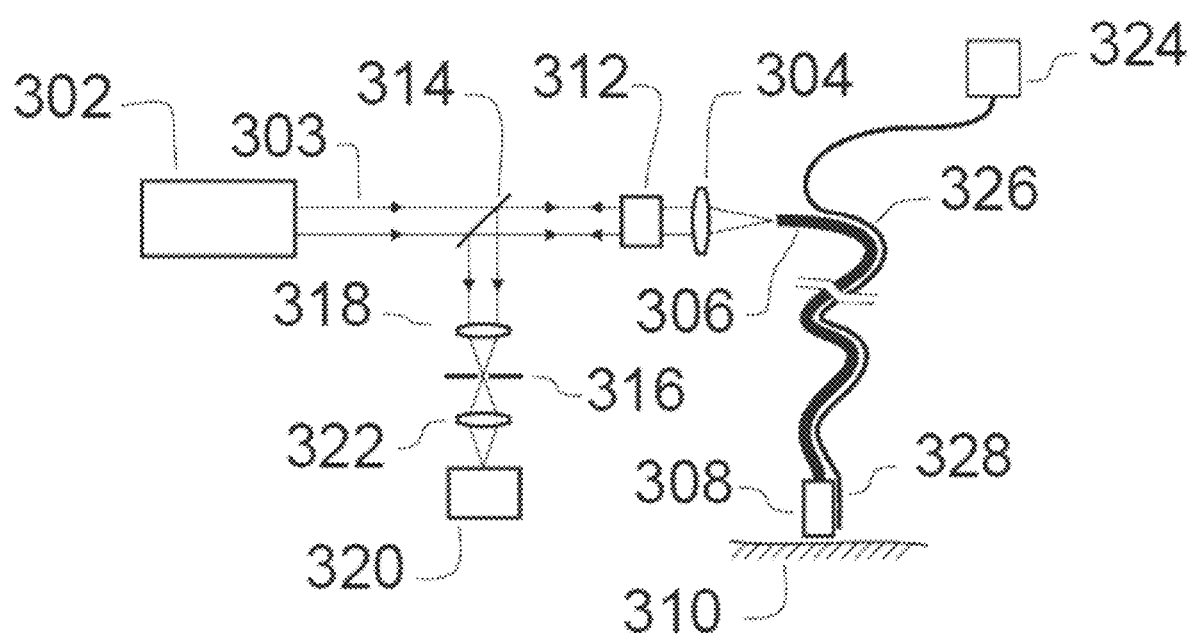
FIG. 10 illustrates a schematic representation of an apparatus for ion channel activity measurement using a fiber optic delivery system, in accordance with some embodiments of the present disclosure.

In some embodiments of the cellular ionic activity visualization system the graded index lens 286 can be incorporated into a laparoscopic or cannula-based instrument for observation deep within the body. FIG. 10 provides a schematic representation of a scope based or cannula-based imaging system and apparatus utilizing a fiber optic imaging system 300. Optical source 302 provides an optical beam 303 (which is shown here as collimated departing the optical source 302 but which can be collimated external to the optical source 302) which is focused by first focusing element 304 into fiber optic cable 306 which transports light via second focusing element 308 into tissue 310 under investigation. Optical scanning element 312 can optionally be employed to direct the optical beam 303 into the fiber optical cable. Once delivered to the tissue 310 the scattered light captured by the imaging lens (e.g., the second focusing element 308) is transmitted back up the fiber retracing its path before being reflected from beam splitter 314, focused through pinhole 316 by third focusing element before being either imaged or simply directed onto detector 320 by fourth focusing element 322.

In some embodiments, optical source 302 is a laser, laser diode, wavelength tunable laser, broadband optical source or other optical source capable of delivering light of a suitable intensity and spectral content for the intended application. Fiber optic cable 306 can be a single-mode fiber, a multi-mode fiber or a cable containing a plurality of cores of single- or multi-mode fibers. Optical scanning element 312 can be an inline electro-optic or acousto-optic beam steering modulator, a scanning mirror assembly containing one or more than one mirror or some other beam steering device. Beam splitter 324 can be a partially reflecting mirror or a polarizing beam splitter in which case the optical source can need to be polarized.

In one embodiment, detector 320 is a simple photodiode, avalanche photodiode or other single element photosensitive device. In some embodiments, the detection system can utilize such a device as a reverse biased photodiode detector for use as the input stage of a transimpedance amplifier. In such embodiments, the fourth focusing element 322 in FIG. 10 is not required if the detector 320 is large enough to accept the light that passes through pinhole 316.

In yet another embodiment, detector 320 is a linear array of single detection elements or a two-dimensional array of detection elements. The individual detection elements can be Charge Coupled Device (CCD) detector elements of other photosensitive elements.

In some embodiments, a plurality of fibers or cores are used in a fiber optic cable, the distal end of which are each imaged onto a different adjacent region within the tissue 288 under investigation as shown in FIG. 9. In such embodiments, the fibers are illuminated at the same time with each adjacent fiber probing a different but adjacent region within the tissue. The light captured by second focusing element 308 in FIG. 10 that returns from the tissue 310 travels back through the system and is reflected by beam splitter 314 toward the detector 320. The optical system employed here using a plurality of tightly bundled fiber cores allows the adjacent regions within the tissue 310 to be imaged onto the detector 320. In some embodiments, a two-dimensional CCD array is used the detection element.

In some embodiments, system 300 includes a fluorescent dye delivery system including dye reservoir and pressurized dosing apparatus, delivery tube 326 and delivery nozzle 328. Delivery tube 326 can be combined with a fiber optic cable in the scope based or cannula-based delivery device in order to deliver fluorescent dye directly to the site under investigation. Delivery nozzle 328 can deliver measured doses of fluorescent dye directly underneath the second focusing element 308 and into the field of view of the instrument.

In some embodiments, optical scanning element 312 can be used to sequentially deliver optical beam 303 into one of a plurality of cores of a multi-core or multi-fiber optical fiber delivery means. The act of sequentially illuminating each of the cores 284, 284' etcetera provides the mechanism for scanning across the sample as described in the discussion of FIG. 9.

In some embodiments, second focusing element 308 can be a graded index lens or a different type of optical imaging system which might include without limitation a conventional optical lens system including one or more lenses.

The cellular ionic activity visualization system can include optical, magnetic and electrochemical ion channel monitoring means as well as optical and non-optical treatment means. While it can be obvious to those of ordinary skill in the art that an optical monitoring means many be combined with an optical treatment means and non-optical monitoring means can be combined with non-optical treatment means, those skilled in the art can appreciate that optical monitoring means can be combined with non-optical treatment means and non-optical monitoring means can also be combined with optical treatment means.

The normal or required conduction pathways can be reinstated in a biological sample using a device which maps the electrical pathways and then intervenes to block unwanted pathways. In some embodiments, a treatment device 262 is located at interstitial locations within the array of ion channel monitoring devices 244. It can be readily apparent to those skilled in the art that there need not be a treatment device 262 at interstitial locations within the array of ion channel monitoring devices 244. In another embodiment, treatment devices 262 are located at a chosen number of such interstitial locations based on the specific application.

Figure 11A:
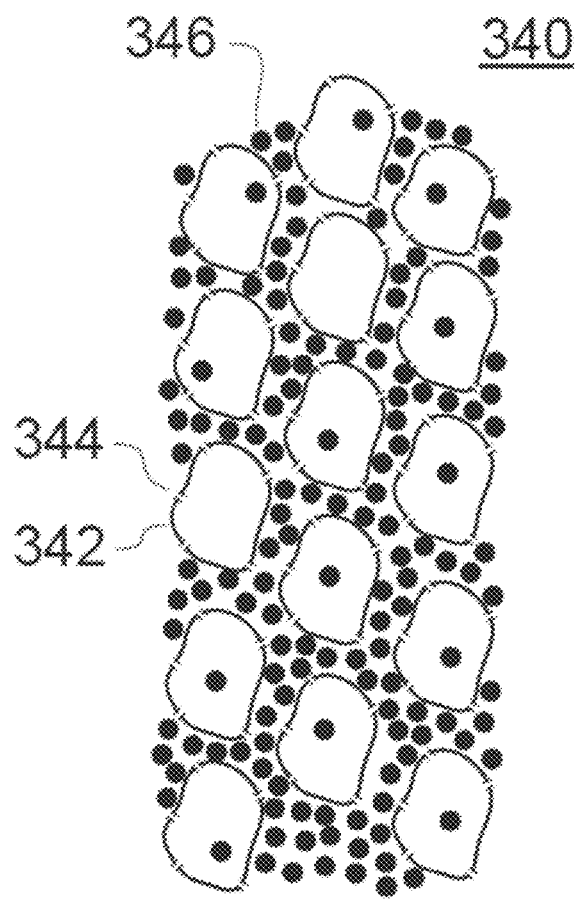
FIG. 11A illustrates a schematic representation of a plurality of cells wherein the majority of the ions of a given species are in the extracellular medium.

FIG. 11(A) shows a schematic representation of a plurality of cells wherein the majority of the ion species of interest are contained within the extracellular medium 340. Each of the plurality of cells 342 contain a plurality of ion channels 344 and ion species 346 are contained both within and without the cell 342. In the example, the intracellular ion concentration is low as shown by a lower density of ion species 346 within the cells 342.

Figure 11B:
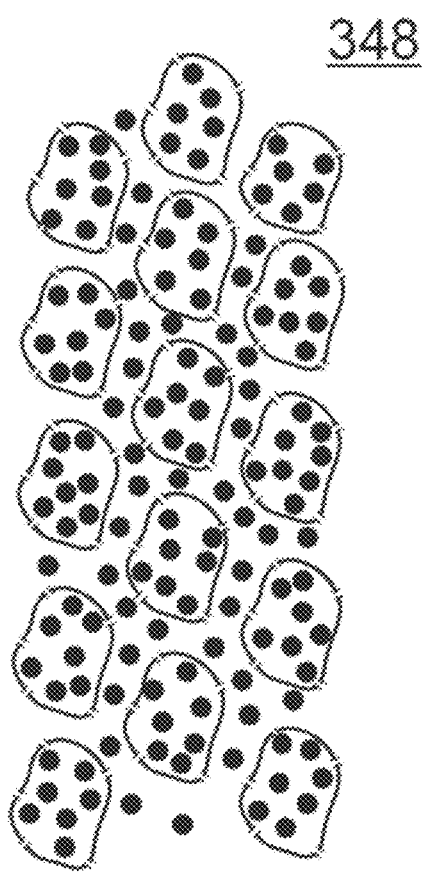
FIG. 11B illustrates a schematic representation of a plurality of cells wherein the majority of the ions of a given species are within the cells.

Conversely, FIG. 11(B) shows a schematic representation of the same plurality of cells wherein the majority of the ion species of interest are contained within the cells 348. While the two diagrams can appear quite similar in their distribution of ions at first glance, optical pattern recognition techniques can determine quite striking differences between the examples. For example, if you were to squint your eyes while looking at both images, the areas of low concentration can appear quite white by comparison to the highly populated regions which can appear quite dark. This is because you lose detail recognition while squinting and gross structural order becomes more obvious. Such a simple visual example demonstrates how optical filtering and pattern recognition can be used to provide a clearer measure of ion species distribution because it can be constructed to search only for gross structure and ignore detail (or vice versa as the application dictates).

The cellular ionic activity visualization system can include an optical spatial filtering technique to identify the concentration distribution of ions in a cellular field of view. Optical pattern recognition allows feature of an image to be extracted from what can otherwise be a noisy image. This is akin to the example of FIG. 8 where squinting your eyes allows you to observe gross structural features rather than being distracted by the detail. Again, using the example of FIG. 8 the gross structural order becomes a series of dark vertical parallel bands (assuming high ion concentration means darker) with lighter bands in between. While these are not straight edged bands, they do however represent gross structural order that can be detected with optical pattern matching.

One approach among many to bar and line detection applies two-dimensional Gabor filters selective to bars of a given thickness and orientation. A Gabor function can be viewed as a sinusoidal plane modulated by a Gaussian envelope. Using different values for bar separation, variance of Gaussian filter and orientation, one can design a filter that is responsive to bars of a given thickness and orientation—which can ultimately match that expected from the tissue under investigation. It can be easy to modify the parameters of the filter to tune into the thickness and orientation of the bands in an automated manner, scanning through the parameters until the system is tuned to the tissue sample under investigation.

Figure 12:
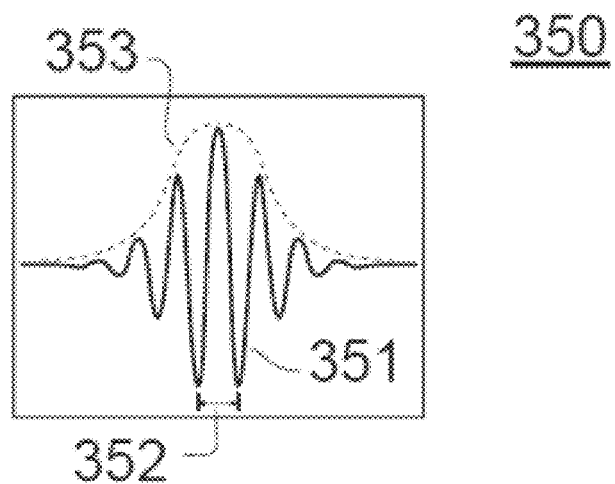
FIG. 12 illustrates a schematic representation of a Gabor filter function.

FIG. 12 shows a schematic representation 350 of the Gabor filter function. Gabor filter function 351 is a sinusoid of period 352 modulated by a Gaussian envelope 353.

Figure 13:
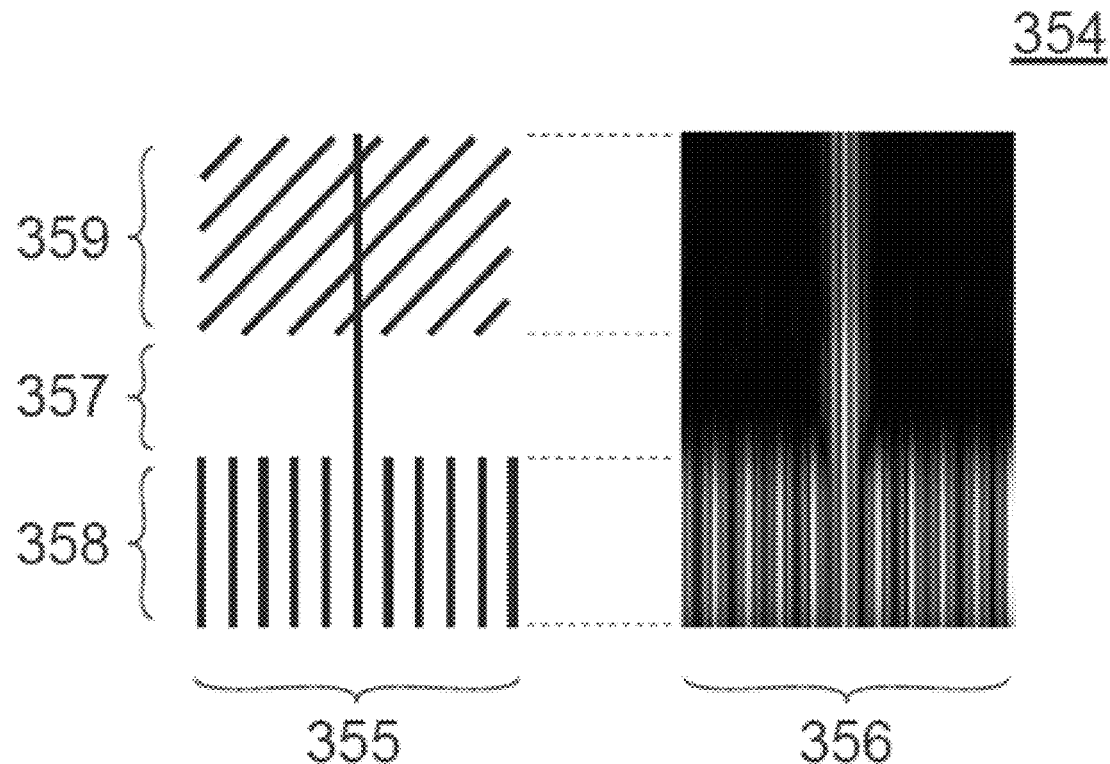
FIG. 13 illustrates a schematic representation of a Gabor filter function applied to a series of bars.

FIG. 13 shows a schematic representation 354 of the application of a Gabor filter function to a series of bars. A Gabor filter is applied to the image under inspection or image plane 355 and the output of the Gabor filter is shown at output plane 356. The image plane 355 contains a series of dark bars on a light background, where each bar is of the same width in order to simplify the discussion. Image segment 357 contains one vertical bar of a defined width, image segment 358 contains a series of identical vertical bars of the same width, while image segment 359 contains one vertical bar of the same width and a series of identical bars of the same width aligned at an angle to the vertical, the angle being roughly 45 degrees.

A Gabor filter optimized to detect a bar of the width and aligned in the vertical direction is applied to the image plane 355. Output plane 356 shows the result of the defined Gabor filter across each image segment 357 through 359. Output plane 356 corresponding to image segment 357 shows one clear detection of a bar corresponding to the position of the bar in the image segment 357 (which can be an image plane segment). Similarly output plane 356 corresponding to image segment 358 shows a series bars detected at the bar spacing in the image segment 358 (which can be an image plane segment). Meanwhile output plane 356 corresponding to image segment 359 shows only one clear detection of a bar—this being at the location of the vertical bar in the image segment 359. None of the series of bars oriented at an angle to the vertical were detected by the vertically aligned Gabor filter. Interestingly the strength of the detection, shown as the 'brightness' of the detection signal corresponding to image segment 359 is less than that for detection of a single vertical bar shown in image segment 357. The weaker response of the Gabor filter is a result of the less well-defined edges of the vertical bar in image segment 359 caused by the intersection of the vertical bar and the series of bars oriented at an angle to the vertical bar. The example shows that such a suitably aligned Gabor filter is suitable for detecting substantially straight edged bars with the response (intensity of the output signal) being proportional to the definition of the edge of the bar.

In a practical sense an optical image containing substantially linear regions of high and low intensity of a certain width can be detected using a Gabor filter. An optical image corresponding to that presented at FIG. 8(A) can present as a positive result if analyzed by a suitably defined Gabor filter but with a strength of that result corresponding the 'sharpness' of the edges of the bands—as seen visually by squinting your eyes as discussed previously.

It can be understood by those skilled in the art that the Gabor filter is one of many such analytical or image processing techniques that can be applied to a given field and any of those filters or techniques are intended to be applied according to the techniques of the cellular ionic activity visualization system.

Figure 14:
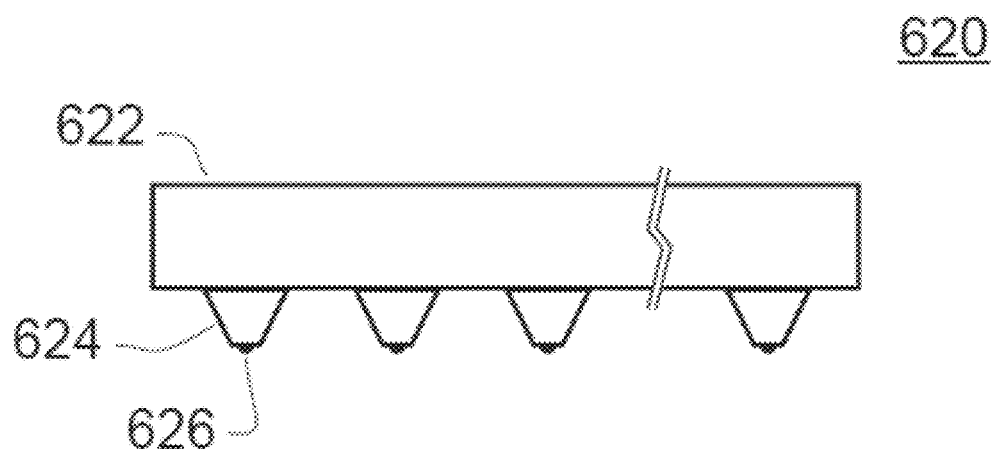
FIG. 14 illustrates a schematic representation of a microscopic device for determining the electrical potential of a biological tissue sample, in accordance with some embodiments of the present disclosure.

The cellular ionic activity visualization system also can include a method of determining the flow of electrical current through a biological tissue sample using an array of microscopic probes. FIG. 14 shows a schematic representation of an apparatus 620 for measuring the electrical potential across a plurality of cells. Microscopic device 622 contains an array of probes 624 in either a one-dimensional array or a two-dimensional array. Probe 624 is electrically largely insulating while the electrically conductive tip 626 is exposed and is the potential sampling point for probe 624. In some embodiments, the plurality of probes 624 are constructed on a substrate and are of a scale whereby more than one probe 624 is in contact with a given cell in the tissue under investigation.

Figure 15:
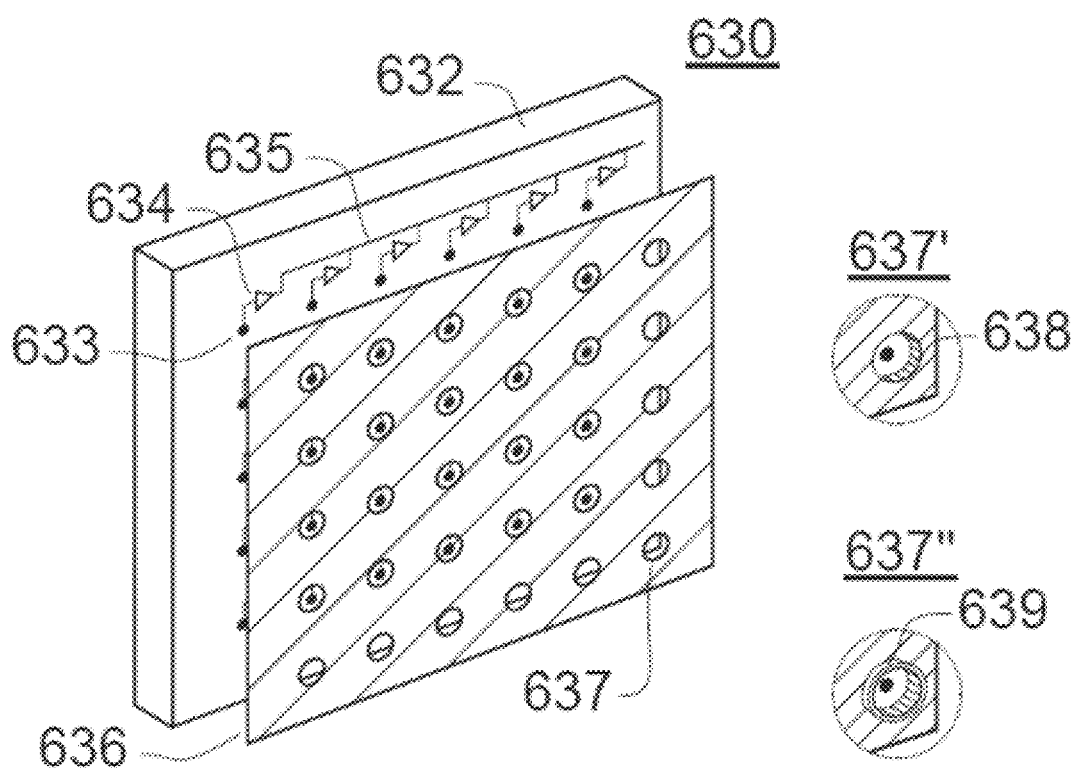
FIG. 15 illustrates a schematic representation of another microscopic device for determining the electrical potential of a biological tissue sample, in accordance with some embodiments of the present disclosure.

FIG. 14 shows a device wherein the conductive tip 626 of each probe 624 sits proud of the surface of the device. Another embodiment allows for the conductive tips of the probes to sit flush with the surface of the device. FIG. 15 shows a schematic representation of another apparatus 630 for measuring the electrical potential across a plurality of cells. Microscopic device includes is substrate 632 that contains a plurality of electrically conductive probes 633 each of which is attached to an electronic circuit 634 for buffering and transferring the measurement to a bus 635. A nonconductive mask layer 636 is applied over the substrate 632 containing an array of voids (e.g., see void 637) matching the location of each of the electrically conductive probes 633. In some embodiments, the nonconductive mask layer 636 includes a physical layer that creates a small enclosed volume around the ion concentration sensor.

A substantially flat microscopic device can be constructed that allows electrical sampling of the cell wall potential across an array of points with a very small inter-probe distance.

The nonconductive mask layer 636 can be constructed with thickness 638 such that the void 637' encompasses a known volume as shown in FIG. 15. In some embodiments, the apparatus can provide a microscopic array of ion sampling cells each of which can constitute the device taught in FIG. 6 which is electrochemical probe 220. It can be evident to one skilled in the art that the diameter of each void and the chosen thickness of the mask layer can allow one to tailor an enclosed volume specific to a range of tissue types and applications; as could the inter-probe spacing.

In another embodiment, the nonconductive mask layer 636 can be constructed with a ring protruding from the surface (the protrusion 639) and encompassing the void 637" as shown in FIG. 15. The thickness of the nonconductive mask layer 636 and length of the protrusion 639 are combined with the area of the void to define the known volume. Such a microscopic structure can be created with chemical deposition, vapor deposition, surface etching, photo masks or any other common microfabrication technique to create a structure that provides a positive pressure contact seal against the cell wall to encompass a known volume of extracellular medium. It can be evident to those skilled in the art that the shape of the protrusion can be adjusted to best suit the application. The void can be circular, square or any other shape and the profile of the protrusion can include without limitation a flat top profile (e.g., see void 637') or top hat profile (e.g., see void 637"), a rounded top protrusion, a knife edge protrusion or any other suitable profile.

Figure 16:
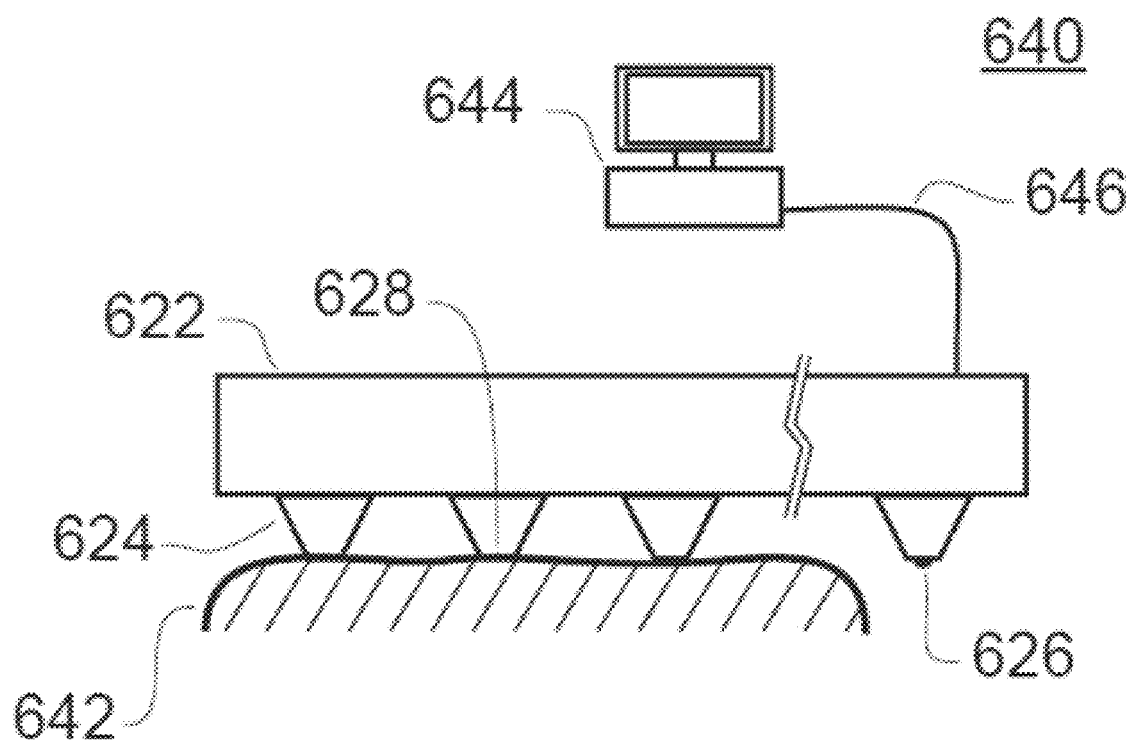
FIG. 16 illustrates a schematic representation of an apparatus used to measure the potential across a biological tissue sample, in accordance with some embodiments of the present disclosure.

FIG. 16 shows a schematic representation of the microscopic device 622 shown in FIG. 14 used to measure the potential across a biological tissue sample where the same numbering has been used for identical elements, in a sensor detection arrangement 640.

Microscopic device 622 is attached to computer system 644 by electrical cabling 646. Microscopic device 622 is brought into contact with biological sample, a cell of which 642 is shown. The dimensions of the electrically conductive tip 626 is chosen such that upon contact with the cell wall 642 it is encased by the cell wall and is not in contact with the intercellular medium. The electrically conductive tip is only in contact with the cell wall and insulated from the intercellular medium by the body of the probe 624, measuring only the potential of the cell wall 642 at the contact point.

In some embodiments, the microscopic device 622 is delivered to the tissue under investigation via scoped or keyhole surgical instruments or through a cannula or some other delivery means. In some embodiments, a plurality of such microscopic devices are delivered to the site and the electrical potential map is 'stitched' together by the computer system 644, wherein the plurality of devices can be adjacent to one another, separated by some distance, delivered in an array or even simultaneously spanning exterior and interior surfaces of an organ such as but not limited to the myocardium.

Figure 17:
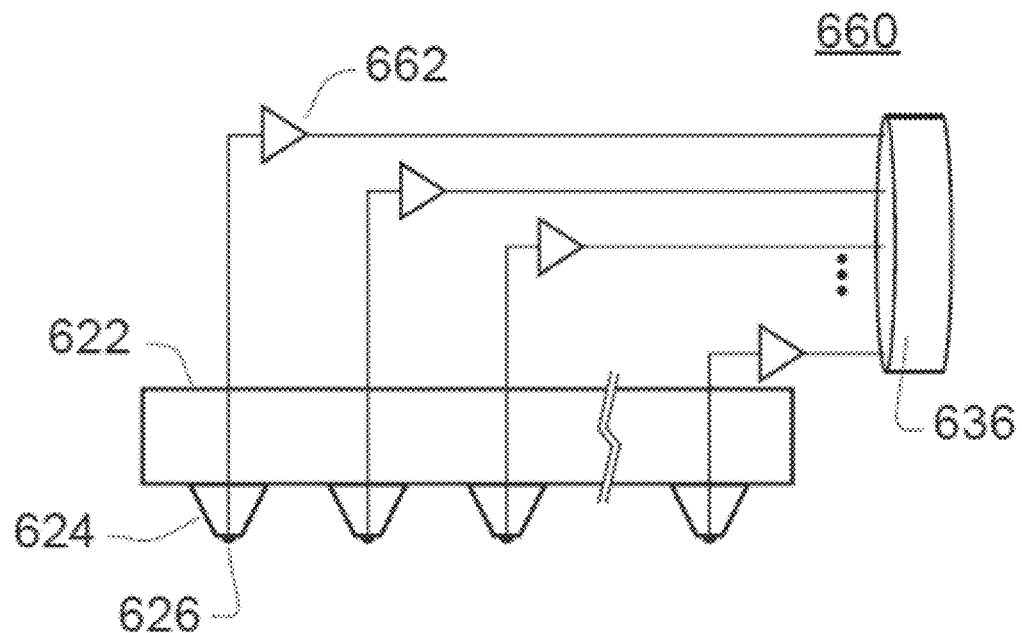
FIG. 17 illustrates a schematic representation of a sensor detection arrangement for sampling a plurality points and transferring measurements to an external computer system, in accordance with some embodiments of the present disclosure.

FIG. 17 is a schematic representation of sensor detection arrangement 660 for microscopic device 622 where the same numbering has been used for identical elements in previous figures. Microscopic device 622 with a plurality of electrical potential sampling points (e.g., see conductive tip 626) is connected to an external computer system via nonconductive mask layer 636 and/or electrical cabling. Each of the sampling points are connected to an electronic circuit 662 for buffering and transferring each measurement to an external computer via nonconductive mask layer 636 and/or electrical cabling.

Figure 18:
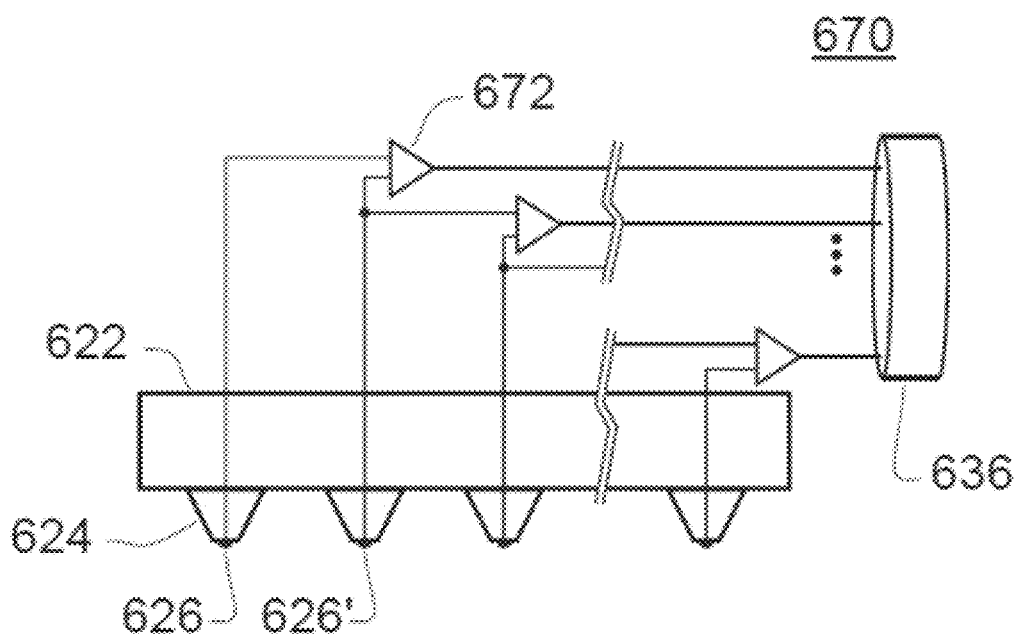
FIG. 18 illustrates a schematic representation of a sensor detection arrangement for providing a differential measurement across a plurality of adjacent sampling points and transferring measurements to an external computer system, in accordance with some embodiments of the present disclosure.

A further embodiment is taught in FIG. 18 of a sensor detection arrangement 670 wherein adjacent conductive tips 626 and 626' are fed into a difference circuit 672 that provides a signal to the external computer via nonconductive mask layer 636 and/or electrical cabling, which can be representative of the difference in electrical potential between adjacent conductive tips 626 and 626'. It can be obvious to those skilled in the art that the techniques taught in FIGS. 17 and 18 are applicable and intended to be combined with other techniques taught in the cellular ionic activity visualization system including without limitation the devices taught in FIG. 15.

Figure 19:
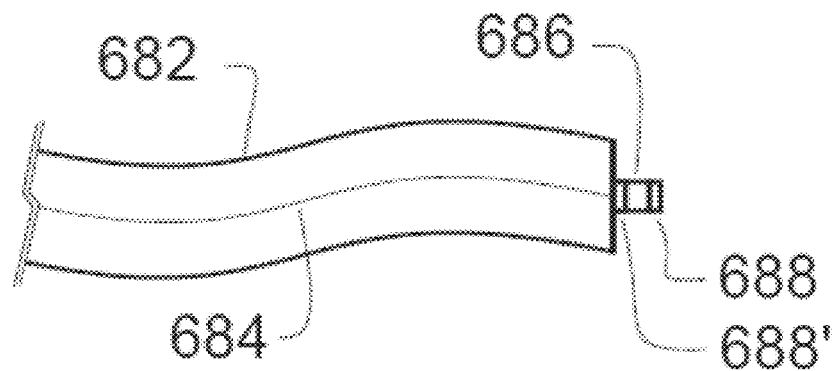
FIG. 19 illustrates a schematic representation of a diamond NV center detection apparatus, in accordance with some embodiments of the present disclosure.

FIG. 19 is a schematic representation of a diamond NV center detection apparatus 680 according to the cellular ionic activity visualization system. Fiber optic cable 682 contains a core 684 with magnetic field sensitive diamond NV center 686 attached thereto.

In some embodiments, diamond NV center 686 is sandwiched between optically reflective coatings 688 and 688' to provide an optical cavity for increasing the optical field strength in the diamond NV center 686. In another embodiment, the coating 688' is not employed and of course the apparatus can be employed without any of the reflective coatings 688 or 688'.

Figure 20:
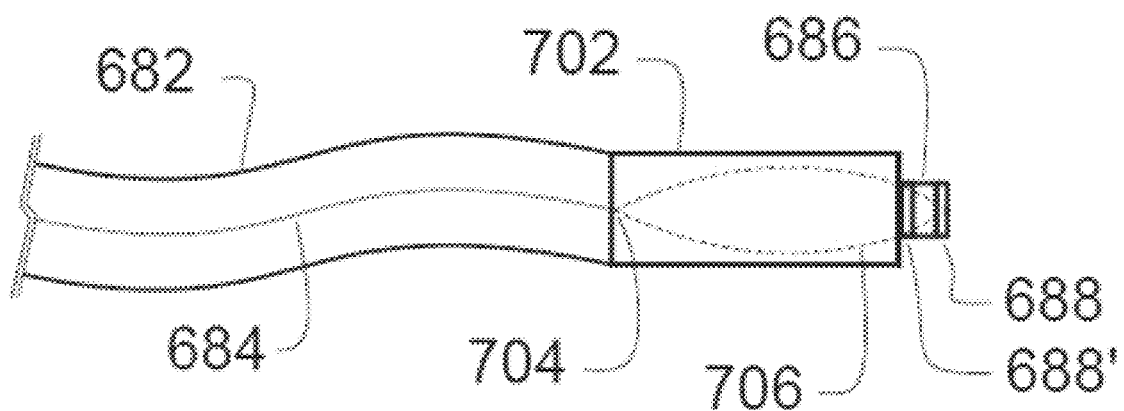
FIG. 20 illustrates a schematic representation of a further diamond NV center detection apparatus, in accordance with some embodiments of the present disclosure.

FIG. 20 is a schematic representation of another embodiment of a diamond NV center detection apparatus, apparatus 700, with parts somewhat similar to parts of the diamond NV center detection apparatus 680 utilizing the same numbering. Graded index lens 702 is attached to the distal end of fiber optic cable 682. Light emitted from the distal end of the core 704 traces a path 706 in the graded index lens. Diamond NV center 686 is attached to the distal end of the graded index lens and, in some embodiments, is sandwiched between reflective coatings 688 and 688' (which can be reflective cavity mirrors), although these can be applied as selected.

Some embodiments of the cellular ionic activity visualization system can include a network of computer systems which can include on one or more server computers. The network of computer systems can also include client devices that can communicated data with the server computer(s). The network of computer systems can also include one or more LAN/WAN networks which can communicatively couple computing devices in the network. The LAN/WAN network(s) can include one or more local area networks (LAN(s)) or one or more wide area networks (WAN(s)). The LAN/WAN network(s) can include the Internet or any other type of interconnected communications network. The LAN/WAN network(s) can also include a single computer network or a telecommunications network. More specifically, the LAN/WAN network(s) can include a local area network (LAN) such as a private computer network that connects computers in small physical areas, a wide area network (WAN) to connect computers located in different geographical locations, or a metropolitan area network (MAN)—also known as a middle area network—to connect computers in a geographic area larger than that covered by a large LAN but smaller than the area covered by a WAN.

At least each component of the network of computer systems can be or include a computer system which can include memory that can include media. The media can include or be volatile memory components, non-volatile memory components, or a combination of such. In general, each of the computer systems can include a host system that uses the memory. For example, the host system can write data to the memory and read data from the memory. The host system can be a computing device such as a desktop computer, laptop computer, network server, mobile device, or such computing device that includes a memory and a processing device. The host system can include or be coupled to the memory so that the host system can read data from or write data to the memory. The host system can be coupled to the memory via a physical host interface. The physical host interface can provide an interface for passing control, address, data, and other signals between the memory and the host system.

Example aspects of an example computer system, in accordance with some embodiments of the present disclosure, can include parts of the computer system within which a set of instructions, for causing the machine to perform any one or more of the methodologies discussed herein, can be executed. In some embodiments, the computer system can correspond to a host system that includes, is coupled to, or utilizes memory or can be used to perform the operations of a controller. In alternative embodiments, the machine can be connected (e.g., networked) to other machines in a LAN, an intranet, an extranet, or the Internet. The machine can operate in the capacity of a server or a client machine in client-server network environment, as a peer machine in a peer-to-peer (or distributed) network environment, or as a server or a client machine in a cloud computing infrastructure or environment.

The machine can be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

An example computer system disclosed herein can include a processing device, a main memory (e.g., read-only memory (ROM), flash memory, dynamic random-access memory (DRAM), etc.), a static memory (e.g., flash memory, static random-access memory (SRAM), etc.), and a data storage system, which communicate with each other via a bus.

The processing device can include one or more general-purpose processing devices such as a microprocessor, a central processing unit, or the like. More particularly, the processing device can be a microprocessor or a processor implementing other instruction sets, or processors implementing a combination of instruction sets. The processing device can also include one or more special-purpose processing devices such as an application specific integrated circuit (ASIC), a field programmable gate array (FPGA), a digital signal processor (DSP), network processor, or the like. The processing device can be configured to execute instructions for performing the operations discussed herein. The computer system can further include a network interface device to communicate over LAN/WAN network(s).

The data storage system can include a machine-readable storage medium (also known as a computer-readable medium) on which is stored one or more sets of instructions or software embodying any one or more of the methodologies or functions described herein. The instructions can also reside, completely or at least partially, within the main memory or within the processing device during execution thereof by the computer system, the main memory and the processing device also constituting machine-readable storage media.

In one embodiment, the instructions include instructions to implement functionality corresponding to aspect of the network of devices disclosed herein. While the machine-readable storage medium can be a single medium, the term "machine-readable storage medium" should be taken to include a single medium or multiple media that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media, and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a predetermined selected result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that these and similar terms are to be associated with the appropriate physical quantities and are merely convenient labels applied to these quantities. The present disclosure can refer to the action and processes of a computer system, or similar electronic computing device, that manipulates and transforms data represented as physical (electronic) quantities within the computer system's registers and memories into other data similarly represented as physical quantities within the computer system memories or registers or other such information storage systems.

The present disclosure also relates to an apparatus for performing the operations herein. The apparatus can be specially constructed for the intended purposes, or it can include a general-purpose computer selectively activated or reconfigured by a computer program stored in the computer. Such a computer program can be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general-purpose systems can be used with programs in accordance with the teachings herein, or it can prove convenient to construct a more specialized apparatus to perform the method. The structure for a variety of these systems will appear as set forth in the description below. In addition, the present disclosure is not described with reference to any particular programming language. It will be appreciated that a variety of programming languages can be used to implement the teachings of the disclosure as described herein.

The present disclosure can be provided as a computer program product, or software, that can include a machine-readable medium having stored thereon instructions, which can be used to program a computer system (or other electronic devices) to perform a process according to the present disclosure. A machine-readable medium includes any mechanism for storing information in a form readable by a machine (e.g., a computer). In some embodiments, a machine-readable (e.g., computer-readable) medium includes a machine (e.g., a computer) readable storage medium such as a read only memory ("ROM"), random access memory ("RAM"), magnetic disk storage media, optical storage media, flash memory components, etc.

In the foregoing specification, embodiments of the disclosure have been described with reference to specific example embodiments thereof. It will be evident that various modifications can be made thereto without departing from the broader spirit and scope of embodiments of the disclosure as set forth in the following claims. The specification and drawings are, accordingly, to be regarded in an illustrative sense rather than a restrictive sense.

The invention claimed is:

1. An apparatus, comprising:
a laparoscopic instrument;
an optical source configured to emit an optical beam;
a focusing element configured to focus the optical beam into a fiber optic cable; and
a fiber optic delivery system, configured to be integrated into the laparoscopic instrument and provide ion channel activity measurement, and the fiber optic delivery system comprising the fiber optic cable, a fiber optic core, and a graded index lens,
wherein the fiber optic cable comprises the fiber optic core,
wherein the graded index lens is configured to:
contact a biological sample;
focus a ray of light on the biological sample, wherein the ray of light is emanating from the fiber optic core; and collect light to produce an image of an interface at the graded index lens and the biological sample; and wherein the fiber optic core is configured to:

transmit light to the graded index lens; and filter backscattered light reflected from the biological sample to select light from a field plane within the biological sample, wherein the focusing element is a first light focusing element and the graded index lens is a second light focusing element, and further comprising an optical scanning element configured to direct the optical beam into the fiber optic cable, wherein the graded index lens is configured to capture scattered light in its production of the image of the interface at the graded index lens and the biological sample, and wherein the scattered light captured by the graded index lens is transmitted via an optical fiber of the fiber optic cable;

further comprising a beam splitter, and wherein the scattered light, transmitted via the optical fiber, retraces a path of the optical beam before being reflected by the beam splitter; and further comprising a pinhole and a third focusing element that is configured to focus the scattered light through the pinhole after the scattered light has been reflected by the beam splitter.

2. The apparatus of claim 1, further comprising a computer system configured to determine a state and activity of ionic channels of a plurality of cells in the biological sample based on the image of the interface at the graded index lens and the biological sample.

3. The apparatus of claim 1, wherein the fiber optic cable comprises a plurality of fiber optic cores, wherein the plurality of fiber optic cores includes the fiber optic core, and wherein the graded index lens is configured to:

focus rays of light on the biological sample emanating from the plurality of fiber optic cores, wherein each one of the rays of light is emanating from a respective fiber optic core of the plurality of fiber optic cores; and produce respective images of respective interfaces at the graded index lens and the biological sample for each respective fiber optic core of the plurality of fiber optic cores to provide spatial discrimination within the biological sample; and wherein each fiber optic core of the plurality of fiber optic cores is configured to:

transmit light to the graded index lens; and filter backscattered light reflected from the biological sample to select light from a respective field plane within the biological sample.

4. The apparatus of claim 3, further comprising a computer system configured to determine a state and activity of ionic channels of a plurality of cells in the biological sample, based on the respective images of the respective interfaces at the graded index lens and the biological sample for each respective fiber optic core of the plurality of fiber optic cores.

5. The apparatus of claim 4, wherein the fiber optic delivery system is in a confocal arrangement.

6. The apparatus of claim 1, wherein the optical beam emitted from the optical source is a collimated optical beam.

7. The apparatus of claim 1, wherein the light focused through the pinhole is used as input for the production of the image of the interface at the graded index lens and the biological sample.

8. The apparatus of claim 1, further comprising a fourth focusing element configured to direct the light focused through the pinhole onto a light detector of the apparatus.

9. The apparatus of claim 1, wherein the fiber optic core comprises a magnetic field sensitive diamond nitrogen-vacancy (NV) center.

10. The apparatus of claim 9, wherein the magnetic field sensitive diamond NV center is sandwiched between optically reflective coatings to provide an optical cavity for increasing optical field strength in the magnetic field sensitive diamond NV center.

11. The apparatus of claim 10, wherein the magnetic field sensitive diamond NV center is attached to a distal end of the graded index lens.

12. A system, comprising:

a laparoscopic instrument;

an array of microscopic probes, integrated into or delivered through the laparoscopic instrument, and configured to measure electrical potential across a plurality of cells of a biological sample;

an optical source configured to emit an optical beam;

a focusing element configured to focus the optical beam into a fiber optic cable; and a fiber optic delivery system, configured to be integrated into the laparoscopic instrument and provide ion channel activity measurement, and the fiber optic delivery system comprising the fiber optic cable, a fiber optic core, and a graded index lens, wherein the fiber optic cable comprises the fiber optic core, wherein the graded index lens is configured to:

contact the biological sample;

focus a ray of light on the biological sample, wherein the ray of light is emanating from the fiber optic core; and collect light to produce an image of an interface at the graded index lens and the biological sample; and wherein the fiber optic core is configured to:

transmit light to the graded index lens; and filter backscattered light reflected from the biological sample to select light from a field plane within the biological sample; and further comprising a computer system configured to determine a state and activity of ionic channels of the plurality of cells in the biological sample based on the measured electrical potential across the plurality of cells of the biological sample and the image of the interface at the graded index lens and the biological sample.

13. The system of claim 12, further comprising a microscopic device comprising the array of microscopic probes and wherein respective conductive tips of the array of microscopic probes sit flush with a surface of the microscopic device.

14. An apparatus, comprising:

a laparoscopic instrument;

an optical source configured to emit an optical beam;

a focusing element configured to focus the optical beam into a fiber optic cable; and a fiber optic delivery system, configured to be integrated into the laparoscopic instrument and provide ion channel activity measurement, and the fiber optic delivery system comprising the fiber optic cable, a fiber optic core, and a graded index lens, wherein the fiber optic cable comprises the fiber optic core, wherein the graded index lens is configured to:
contact a biological sample;
focus a ray of light on the biological sample, wherein the ray of light is emanating from the fiber optic core; and
collect light to produce an image of an interface at the graded index lens and the biological sample; and
wherein the fiber optic core is configured to:
transmit light to the graded index lens; and
filter backscattered light reflected from the biological sample to select light from a field plane within the biological sample,
wherein the fiber optic core comprises a magnetic field sensitive diamond nitrogen-vacancy (NV) center, and
wherein the magnetic field sensitive diamond NV center is sandwiched between optically reflective coatings to provide an optical cavity for increasing optical field strength in the magnetic field sensitive diamond NV center.

15. The apparatus of claim 14, further comprising a computer system configured to determine a state and activity of ionic channels of a plurality of cells in the biological sample based on the image of the interface at the graded index lens and the biological sample.

16. The apparatus of claim 14, wherein the fiber optic cable comprises a plurality of fiber optic cores, wherein the plurality of fiber optic cores includes the fiber optic core, and wherein the graded index lens is configured to:
focus rays of light on the biological sample emanating from the plurality of fiber optic cores, wherein each one of the rays of light is emanating from a respective fiber optic core of the plurality of fiber optic cores; and
produce respective images of respective interfaces at the graded index lens and the biological sample for each respective fiber optic core of the plurality of fiber optic cores to provide spatial discrimination within the biological sample; and
wherein each fiber optic core of the plurality of fiber optic cores is configured to:
transmit light to the graded index lens; and
filter backscattered light reflected from the biological sample to select light from a respective field plane within the biological sample.

17. The apparatus of claim 16, further comprising a computer system configured to determine a state and activity of ionic channels of a plurality of cells in the biological sample, based on the respective images of the respective interfaces at the graded index lens and the biological sample for each respective fiber optic core of the plurality of fiber optic cores.

18. The apparatus of claim 17, wherein the fiber optic delivery system is in a confocal arrangement.

19. The apparatus of claim 14, wherein the magnetic field sensitive diamond NV center is attached to a distal end of the graded index lens.

20. The apparatus of claim 14, wherein the focusing element is a first light focusing element and the graded index lens is a second light focusing element.

* * * * *